United States Patent
Müller

(10) Patent No.: US 10,307,350 B2
(45) Date of Patent: Jun. 4, 2019

(54) MORPHOGENETICALLY ACTIVE AMORPHOUS CALCIUM POLYPHOSPHATE NANOPARTICLES FOR THERAPEUTIC APPLICATIONS

(71) Applicant: NanotecMARIN GmbH, Mainz (DE)

(72) Inventor: Werner Ernst Ludwig Georg Müller, Mainz (DE)

(73) Assignee: NANOTECMARIN GMBH, Mainz (DE)

( * ) Notice: Subject to any disclaimer, the term of this patent is extended or adjusted under 35 U.S.C. 154(b) by 0 days.

(21) Appl. No.: 15/527,479

(22) PCT Filed: Nov. 10, 2015

(86) PCT No.: PCT/EP2015/076222
§ 371 (c)(1),
(2) Date: May 17, 2017

(87) PCT Pub. No.: WO2016/078971
PCT Pub. Date: May 26, 2016

(65) Prior Publication Data
US 2017/0319446 A1    Nov. 9, 2017

(30) Foreign Application Priority Data

Nov. 17, 2014  (GB) .................................. 1420363.2
Feb. 9, 2015   (GB) .................................. 1502116.5

(51) Int. Cl.
| | | |
|---|---|---|
| *A61K 31/07* | (2006.01) |
| *A61K 33/42* | (2006.01) |
| *A61K 9/14* | (2006.01) |
| *C01B 25/40* | (2006.01) |
| *A61K 8/24* | (2006.01) |
| *A61L 27/12* | (2006.01) |
| *A61K 8/67* | (2006.01) |
| *A61Q 19/08* | (2006.01) |
| *A61K 8/02* | (2006.01) |

(52) U.S. Cl.
CPC ............. *A61K 8/24* (2013.01); *A61K 8/0283* (2013.01); *A61K 8/671* (2013.01); *A61L 27/12* (2013.01); *A61Q 19/08* (2013.01); *A61K 2800/413* (2013.01); *A61L 2300/624* (2013.01); *A61L 2400/12* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 6,491,899 B1* | 12/2002 | Leinen | .................. | A61K 8/347 424/49 |
| 8,084,060 B2* | 12/2011 | Grover | .................. | A61K 9/143 424/489 |
| 2006/0246016 A1* | 11/2006 | Burzynski | ............ | A61K 8/4926 424/49 |

FOREIGN PATENT DOCUMENTS

| | | |
|---|---|---|
| WO | WO 2008/005509 A2 | 1/2008 |
| WO | WO 2008/006204 A2 | 1/2008 |

* cited by examiner

*Primary Examiner* — Abigail Vanhorn
(74) *Attorney, Agent, or Firm* — Saliwanchik, Lloyd & Eisenschenk

(57) ABSTRACT

This invention concerns a calcium polyphosphate material consisting of amorphous nanoparticles with a diameter of approximately between about 45 nm to about 0.25 μm that displays a considerable hardness (elastic modulus) of about 1.3 GPa. The inventive noncrystalline and biodegradable material that is produced under mild conditions, at room temperature, is morphogenetically active and preferably induces bone formation and the expression of the marker gene for osteoblast activity, alkaline phosphatase. In a preferred aspect, the invention concerns a method for producing amorphous retinol/calcium-polyphosphate nanospheres (retinol/aCa-polyP-NS) that show several unexpected properties and can be used in the treatment or prophylaxis of a variety of dermatological conditions, including photoaging.

18 Claims, 11 Drawing Sheets
Specification includes a Sequence Listing.

MORPHOGENETICALLY ACTIVE AMORPHOUS CALCIUM POLYPHOSPHATE NANOPARTICLES FOR THERAPEUTIC APPLICATIONS

CROSS REFERENCE TO A RELATED APPLICATION

This application is a National Stage Application of International Application Number PCT/EP2015/076222, filed Nov. 10, 2015; which claims priority to Great Britain Application No. 1420363.2, filed Nov. 17, 2014 and Great Britain Application No. 1502116.5, filed Feb. 9, 2015; which are incorporated herein by reference in their entirety.

This invention concerns a calcium polyphosphate material consisting of amorphous nanoparticles with a diameter of approximately between about 45 nm to about 0.25 µm that displays a considerable hardness (elastic modulus) of about 1.3 GPa. The inventive non-crystalline and biodegradable material that is produced under mild conditions, at room temperature, is morphogenetically active and preferably induces bone formation and the expression of the marker gene for osteoblast activity, alkaline phosphatase. In a preferred aspect, the invention concerns a method for producing amorphous retinol/calcium-polyphosphate nanospheres (retinol/aCa-polyP-NS) that show several unexpected properties and can be used in the treatment or prophylaxis of a variety of dermatological conditions, including photoaging.

BACKGROUND OF THE INVENTION

Inorganic polyphosphate (polyP) is a nontoxic polymer existing in a wide range of organisms (Schröder H C, Müller W E G, eds (1999) Inorganic Polyphosphates—Biochemistry, Biology, Biotechnology. Prog Mol Subcell Biol 23:45-81; Kulaev I S, Vagabov V, Kulakovskaya T (2004) The Biochemistry of Inorganic Polyphosphates. New York: John Wiley & Sons Inc). It consists of usually linear molecules of tens to hundreds of phosphate units which are linked together via high energy phosphoanhydride bonds. Living organisms can produce this polymer metabolically at ambient temperatures, while the chemical synthesis of polyP requires high temperatures of several hundred degrees.

PolyP in Bone

Previous studies revealed that polyP molecules of different chain lengths accumulate especially in bone cells (Leyhausen G, Lorenz B, Zhu H, Geurtsen W, Bohnensack R, Müller W E G, Schröder H C. Inorganic polyphosphate in human osteoblast-like cells. J Bone Mineral Res 1998; 13:803-812; Schröder H C, Kurz L, Müller W E G, Lorenz B. Polyphosphate in bone. Biochemistry (Moscow) 2000; 65:296-303). In addition, human osteoblast-like cells contain enzymes that hydrolyze polyP, e.g. the alkaline phosphatase (ALP) (Lorenz B, Schröder H C. Mammalian intestinal alkaline phosphatase acts as highly active exopolyphosphatase. Biochim Biophys Acta 2001; 1547:254-261). PolyP is also found in platelets (Smith S A, Mutch N J, Baskar D, Rohloff P, Docampo R, Morrissey J H. Polyphosphate modulates blood coagulation and fibrinolysis. Proc Natl Acad Sci USA 2006; 103:903-908), possibly playing a role in initiation of healing of bone fractures.

PolyP has an inductive effect on osteoblasts mainly as an anabolic polymer that stimulates differentiation of bone cells and mineralization (reviewed in: Wang X H, Schröder H C, Wiens M, Ushijima H, Müller W E G. Bio-silica and bio-polyphosphate: applications in biomedicine (bone formation). Current Opinion Biotechnol 2012; 23:570-578; Wang X H, Schröder H C and Müller W E G. Enzymatically synthesized inorganic polymers as morphogenetically active bone scaffolds: application in regenerative medicine. Int Rev Cell Mol Biol 2014; 313:27-77). In addition, polyP induces the ALP (Müller W E G, Wang X H, Diehl-Seifert B, Kropf K, Schloßmacher U, Lieberwirth I, Glasser G, Wiens M and Schröder H C. Inorganic polymeric phosphate/polyphosphate as an inducer of alkaline phosphatase and a modulator of intracellular $Ca^{2+}$ level in osteoblasts (SaOS-2 cells) in vitro. Acta Biomater 2011; 7:2661-2671).

Bone Graft Materials

Bone graft materials must be biocompatible and comprise similar biomechanical properties like the physiological bone tissue. Favored are substitutes that are degradable and allow the surrounding tissue to migrate into at least the surface region of the non-self implant to strengthen the bridging of the biofabricated material to the surrounding tissue and to avoid inflammatory reactions.

Besides of cell-based bone graft substitutes ceramic-based materials have proven to be useful bone scaffold for implants. Among the calcium phosphate-based ceramics, the following materials are of particular relevance:

Hydroxyapatite (HA).

HA is produced at a high-temperature reaction and comprises a crystalline form of calcium phosphate (Noshi T, Yoshikawa T, Ikeuchi M, Dohi Y, Ohgushi H, Horiuchi K, Sugimura M, Ichijima K, Yonemasu K. Enhancement of the in vivo osteogenic potential of marrow/hydroxyapatite composites by bovine bone morphogenetic protein. J Biomed Mater Res 2000; 52:621-630). Since the composition of HA is $Ca_{10}(PO_4)_6(OH)_2$ with a calcium-to-phosphate ratio of 1.67 this material is chemically very similar to the mineralized phase of physiological bone. Based on this property HA shows suitable biocompatibility (Nandi S K, Kundu B, Ghosh S K, De D K, Basu D. Efficacy of nano-hydroxyapatite prepared by an aqueous solution combustion technique in healing bone defects of goat. J Vet Sci 2008; 9:183-191).

β-Tricalcium Phosphate (β-TCP).

Similar to HA, the chemical composition $Ca_3(PO_4)_2$ and crystallinity of β-TCP match the ones of the mineral phase of bone; in addition, this material is bioabsorbable and biocompatible (Daculsi G, LeGeros R Z, Heughebaert M, Barbieux I. Formation of carbonate apatite crystals after implantation of calcium phosphate ceramics. Calcif Tissue Int 1990; 46:20-27). TCP implants have been successfully used as synthetic bone void fillers both in orthopedics and in dentistry (Shigaku S, Katsuyuki F. Beta-tricalcium phosphate as a bone graft substitute. Jikeikai Med J 2005; 52:47-54).

Bioactive Glass.

Finally, bioactive glass ceramics ("bioglass") initially developed by Hench et al (Hench L L, Splinter R J, Allen W C, Greenlee T K. Bonding mechanisms at the interface of ceramic prosthetic materials. J Biomed Mater Res Symp 1971; 2:117-141; reviewed in: Chen Q, Roether J A, Boccaccini A R. Tissue engineering scaffolds from bioactive glass and composite materials. In: Ashammakhi N, Reis R, Chiellini F Topics in Tissue Engineering, Vol 4, pp. 1-27, 2008) is not only biocompatible but also osteoconductive and allows bone to bind without any intervening fibrous connective tissue interface (Zhang H, Ye X J, Li J S. Preparation and biocompatibility evaluation of apatite/wollastonite-derived porous bioactive glass ceramic scaffolds. Biomed Mater 2009; 4: 45007). This mineralic glass is frequently used as filling material for bone defects either alone or in combination with autogeneic or allogenic cancellous bone graft (Dorea H C, McLaughlin R M, Cantwell H D, Read R, Armbrust L, Pool R, Roush J K, Boyle C. Evaluation of healing in feline femoral defects filled with cancellous autograft, cancellous allograft or Bioglass. Vet Comp Orthop Traumatol 2005; 18:157-168) or with morphogenetically active inorganic polymers, e.g. polyphosphate [polyp] (Wang X H, Tolba E, Schröder H C, Neufurth M, Feng Q, Diehl-Seifert B, Müller W E G. Effect of bioglass on growth and biomineralization of SaOS-2 cells in hydrogel after 3D cell bioprinting. PLoS ONE 2014; 9:e112497).

Since all of these mineralic implant materials are fabricated at temperatures higher than 700° C. and, in turn, are not, or only at a limited degree, osteoinductive like the bioglass, the inventors developed a new potential biomaterial likewise suitable to be used as bone implant.

Skin Aging and Collagen

The epidermis of human skin is composed of keratinocytes of different proliferation and differentiation state, while the dermis is composed of three major types of cells, the fibroblasts, macrophages, and adipocytes. The most abundant protein in the skin and connective tissue, collagen type I, and the other fibrillar collagens, types III and V, are secreted as procollagens and then enzymatically processed to assemble to the triple helix configuration. The quantity and quality, integrity and biomechanical properties, of collagen decrease during skin aging, often accelerated by external factors (Pandel R, Poljšak B, Godic A, Dahmane R (2013) Skin photoaging and the role of antioxidants in its prevention. ISRN Dermatol 12; 2013:930164). Skin aging can be grouped into: i) Chronological or intrinsic aging, and ii) Solar aging (photoaging). Focusing on the photoaging process, it is well established that the aging skin is characterized by reduced amounts of collagen, accumulation of abnormal elastic fibers and, in parallel, increased quantities of glycosaminoglycans in the upper and mid dermis. The major reason for this imbalance in the extracellular matrix fibrillar meshwork is the occurrence of oxygen-derived species including free radicals (Gilchrest B A, Bohr V A. Aging process, DNA damage, and repair. FASEB J 1997; 11:322-330).

While the synthesis of collagen I remains almost unchanged in human skin during lifetime, the extent of collagen III formation drastically drops by 70%. The differential regulation of collagen gene expression type I versus type III is understood to some extent. Due to the exceptionally long half-life of collagen, the fibrils undergo nonenzymatic glycation under formation of advanced glycation end products (AGEs), through which several signaling pathways and collagen types I and III gene expression become modulated (Tang M, Zhong M, Shang Y, Lin H, Deng J, Jiang H, Lu H, Zhang Y, Zhang W. Differential regulation of collagen types I and III expression in cardiac fibroblasts by AGEs through TRB3/MAPK signaling pathway. Cell Mol Life Sci 2008; 65:2924-2932).

Retinoids are structurally characterized by a β-ionone ring with a polyunsaturated side chain consisting of four isoprenoid moieties with a terminal alcohol, aldehyde, carboxylic acid or ester group. It is well established that retinoids are beneficial for skin regeneration, reconstitution of the collagen network, and protective against skin aging (reviewed in: Mukherjee S, Date A, Patravale V, Korting H C, Roeder A, Weindl G. Retinoids in the treatment of skin aging: an overview of clinical efficacy and safety. Clin Interv Aging 2006; 1:327-348). In addition, retinol has been proposed to function as a stabilizer for biologically active skin preservatives (Nystrand G, Debois J. Retinol stabilized cleansing compositions; EP 995433 A1).

The application of polyP as a skin preservative is hampered by the fact that the salt Na-polyP is readily dissolved. The approaches to fabricate polyP-containing biomaterials that are more resistant and simultaneously bioactive included a calcination process. However, during those processes polyP is either disintegrated or transformed into a crystalline state and by that becomes inactive (Pilliar R M, Filiaggi M J, Wells J D, Grynpas M D, Kandel R A. Porous calcium polyphosphate scaffolds for bone substitute applications—in vitro characterization. Biomaterials 2001; 22:963-972; Ding Y L, Chen Y W, Qin Y J, Shi G Q, Yu X X, Wan C X. Effect of polymerization degree of calcium polyphosphate on its microstructure and in vitro degradation performance. J Mater Sci Mater Med 2008; 19:1291-1295).

The new materials according to this invention are based on polyP. Previously polyP has also been used, after calcinations, as potential scaffold for bone implants (Pilliar R M, Filiaggi M J, Wells J D, Grynpas M D, Kandel R A. Porous calcium polyphosphate scaffolds for bone substitute applications—in vitro characterization. Biomaterials 2001; 22:963-972; Qiu K, Wan C X, Zhao C S, Chen X, Tang C W, Chen Y W. Fabrication and characterization of porous calcium polyphosphate scaffolds. J Materials Sci 2006; 41:2429-2434; Ding Y L, Chen Y W, Qin Y J, Shi G Q, Yu X X, Wan C X. Effect of polymerization degree of calcium polyphosphate on its microstructure and in vitro degradation performance. J Mater Sci Mater Med 2008; 19:1291-1295; Wang D, Wallace A F, De Yoreo J J, Dove P M. Carboxylated molecules regulate magnesium content of amorphous calcium carbonates during calcification. Proc Natl Acad Sci USA 2009; 106:21511-21516). In all those preparations, polyP had to be subjected to calcination with the result that the polyP chain might be degraded and the exact chain length is impossible to be determined. Furthermore those polyP scaffolds have not been described to act in an osteoinductive manner.

The material according to this invention is a hard amorphous polyP-based biomaterial that is produced at ambient conditions (i.e. at around 20° C.±10° C.) in the presence of a distinctly adjusted concentration of $CaCl_2$. The material obtained comprises a porous scaffold built of spherical, amorphous nanoparticles that are biodegradable and retain the morphogenetic activity of the inorganic polymer.

Thus, in a first aspect thereof, this invention concerns a new morphogenetically active material consisting of calcium polyphosphate (polyP) nanoparticles that are (i) amorphous and (ii) display an unusual hardness not found for calcium polyphosphate materials prepared by state-of-the-art methods. The inventors developed a controlled and slow fabrication process that is performed at room temperature and unexpectedly resulted in the formation of a material showing these properties. The polyP material formed in the presence of $CaCl_2$ at a stoichiometric ratio of around 1 or 2 (phosphate to calcium) is an amorphous powder that is composed of nanospheres with a diameter of approximately between about 45 nm to about 0.25 μm. The inventive material is degradable, in contrast to the Ca-polyP salt prepared by conventional methods which resists hydrolytic cleavage by phosphatases present in medium over longer time periods in cell culture experiments. The polyP nanoparticles that form this nanoparticulate material are termed amorphous Ca-phosphate nanoparticles [aCa-polyP-NP].

The inventors further succeeded to include retinol into these nanoparticles and thereby to fabricate nanospheres, consisting of retinol inclusions encapsulated within CapolyP shells. These nanospheres are termed amorphous Ca-polyP/retinol nanospheres [retinol/aCa-polyP-NS]. The inventors unexpectedly found that this new, inventive material, the retinol/aCa-polyP-NS, causes collagen type III expression in an unexpected high extent, at concentrations at which the single components, retinol and aCa-polyP-NP, are biologically inactive.

The following patent applications on polyP are deemed relevant; GB1406840.7. Morphogenetically active hydrogel for bioprinting of bioartificial tissue. Inventors: Müller W E G, Schröder H C, Wang X H; GB1403899.6. Synergistic composition comprising quercetin and polyphosphate for treatment of bone disorders. Inventors: Müller W E G, Schröder H C, Wang X H.

In a first aspect of the invention, a novel polyphosphate (polyP) material is provided that is characterized by the following properties: a) The material is amorphous (non-crystalline); b) The material has an unusual hardness (e.g., the elastic modulus of the Ca-polyP2 biopolymer according to this invention amounts to approximately 1.3 GPa (in the context of the present invention, "hard" or "hardness" means a value of approximately 1.3 GPa, such as between 0.8 and 1.8 GPa, preferably between 1.0 and 1.6 GPa), close to value measured for trabecular tissue surrounding human bone [6.9 GPa]); and preferably, c) The material consist of nanoparticles with a diameter of about 45 nm to about 0.25 µm (Ca-polyP2 particles according to this invention). Advantageously, the inventive material can be prepared under mild conditions, such as ambient conditions, and particularly at room temperature.

Hardness can be measured using the Brinell and/or Vickers hardness test method, as known to the person of skill.

It was surprisingly found, that the inventive material is amorphous (non-crystalline), morphogenetically active, it induces bone alkaline phosphatase activity and new bone formation (hydroxyapatite synthesis); and that the material is biodegradable (e.g. by polyphosphatases, such as bone alkaline phosphatase).

This inventive material, whose properties make it superior compared to conventional polyphosphate preparations for a use, for example, in bone regeneration and replacement materials (e.g. GB1406840.7. Morphogenetically active hydrogel for bioprinting of bioartificial tissue [Inventors: Müller W E G, Schröder H C, Wang X H]; GB1403899.6. Synergistic composition comprising quercetin and polyphosphate for treatment of bone disorders [Inventors: Müller W E G, Schröder H C, Wang X H]), can be prepared according to the following method, according to this invention:

a) Dissolution of a polyP salt in water and adjustment of the pH to alkaline values,
b) (slow) Addition of a solution of a calcium salt to the polyP salt (with $Na^+$) solution, and adjustment of the pH to alkaline value, and
c) Collection and drying of the particles thus formed, optionally after washing with ethanol.

This procedure is performed at room temperature.

In another aspect, this invention relates to a method for the fabrication of nanospheres that are composed of (i) $Ca^{2+}$ together with (ii) polyP to form nanoparticles, aCa-polyP-NP, and together with (iii) retinol that is encapsulated by those nanoparticles to form nanospheres.

Unexpectedly, the inventors found that processing of these nanoparticles with retinol and poly(ethylene glycol) [PEG] results in the formation of nanospheres, retinol/aCa-polyP-NS, which show the following unexpected and advantageous properties:

1. The nanospheres according to this invention, retinol/aCa-polyP-NS, are highly homogenous in size (size ~45 nm). This size is optimal for endocytotic cellular uptake (Zhang S, Li J, Lykotrafitis G, Bao G, Suresh S. Size-dependent endocytosis of nanoparticles. Adv Mater 2009; 21:419-424).
2. In contrast, the nanoparticles, aCa-polyP-NP, are large (>50 µm sized) brick-like particles.
3. Both components of the nanospheres, retinol and polyP, act synergistically: if given together at "non-effective" concentrations, a strong increase in proliferation of cells occurs.
4. Both components of the nanospheres, retinol and polyP, cause a highly synergistic effect on the expression of collagen types I and II, and especially collagen type III. The effects are already observed at concentrations of retinol and aCa-polyP-NP that do not display any biological effect if administered alone. Even though the application of retinol at concentrations of ≤1% (36 mM) is assessed as a safe cosmetic ingredient higher concentrations might display adverse effects, e.g. inhibition of responses to viral or chemical carcinogens (see: Final report on the safety assessment of retinol palmitate and retinol. J Americ Coll Toxicol 1987; 6:279-319). Therefore, the nanospheres according to the invention open a more safe application of this compound, e.g. in cosmetics.

The nanospheres according to this invention can be disintegrated by enzymatic hydrolysis in the extracellular space. The main component within the nanospheres, polyP, undergoes degradation by the exo-phosphatase, most likely by the alkaline phosphatase which is involved in the extracellular degradation of polyP (Müller W E G, Wang X H, Diehl-Seifert B, Kropf K, Schloßmacher U, Lieberwirth I, Glasser G, Wiens M, Schröder H C. Inorganic polymeric phosphate/polyphosphate as an inducer of alkaline phosphatase and a modulator of intracellular $Ca^{2+}$ level in osteoblasts (SaOS-2 cells) in vitro. Acta Biomaterialia 2011j; 7:2661-2671). In consequence, not only polyP is released extracellularly but also retinol.

The nanospheres according to this aspect of the invention have the appropriate size to be taken up by a clathrin-mediated endocytosis process. Their biological activity can be blocked with the endocytosis inhibitor triflupromazine. This property of the nanospheres is advantageous under conditions during which the transmembrane retinol transporter is down-regulated (resulting in epidermal thickening).

In consequence, the nanospheres show a dual biological effect of the two active components, polyP and retinol—both via the extracellular route (activation of cell membrane-bound receptors) and via the transmembrane/intracellular route (through endocytosis).

The nanospheres according to this invention are not cytotoxic.

As a preferred example, the method can be carried out using sodium polyphosphate (Na-polyP) as a polyP salt (chain length: 50 phosphate units) in solution and calcium chloride as a calcium salt in solution as follows.

a) Dissolution of 10 g of Na-polyP in 500 ml of distilled water and adjustment of the pH to 10 with 1 M NaOH (room temperature),
b) Slow, dropwise (1 ml/min), addition of a solution of 14 g of calcium chloride (Ca-polyP1) or 28 g of calcium chloride (Ca-polyP2) in 250 ml salt to the Na-polyP solution and adjustment of the pH to 10 (room temperature),
c) Stirring of the thus formed suspension for about 4 h, and
d) Collection of the particles formed, and optionally washing them with ethanol while filtering (0.45 µm filter; e.g., Nalgene Rapid-Flow), and drying at 60° C.

The Ca-polyP material obtained with 14 g of $CaCl_2$ was named Ca-polyP1 (stoichiometric ratio phosphate:calcium of 1); and the Ca-polyP material obtained with 28 g of $CaCl_2$ was named "Ca-polyP2" (stoichiometric ratio phosphate:calcium of 1:2).

The inventive material, consisting of amorphous retinoid/Ca-polyP nanospheres, which are superior compared to the individual (retinoid and polyP) components, can be prepared according to this invention as follows: a) Dissolution of a retinoid and a calcium salt in an organic solvent, b) Slow addition of the retinoid calcium salt solution to an aqueous polyP solution, and c) Collection and drying of the nanospheres formed after washing with water. This procedure is performed at room temperature, under avoidance of light.

As an example, the preparation of the amorphous retinol/Ca-polyP nanospheres (retinol/aCa-polyP-NS) can be carried out using Na-polyP as a polyP salt (chain length: 30 phosphate units) and calcium chloride as a calcium salt as follows. A) Preparation of a solution containing 100 mg of retinol and 2.8 g of $CaCl_2$ in 50 ml absolute ethanol (=Retinol/calcium solution). B) Preparation of a polyP solution containing 1 g of polyP in 100 ml water; in order to avoid a phase separation and to stabilize the emulsion, 2 g of poly(ethylene glycol) [PEG] are added to the Na-polyP solution (=PolyP solution). C) Drop-wise addition of the Retinol calcium solution to the PolyP solution. D) Stirring of the emulsion formed for 6 h. E) Collection of the nanospheres formed by filtration and washing with water to remove excess of calcium ions and unreacted components. F) Drying the particles at room temperature overnight.

The nanoparticles comprising or consisting of the inventive Ca-polyP material are characterized by a high hardness (about 1.3 GPa; Ca-polyP2) compared to larger particles that are produced at a different phosphate to calcium ratio in solution or at harsh reaction conditions, e.g. in acid-flux of phosphoric acid with $Ca(OH)_2$ at high (250° C.) temperature (Jackson L E, Kariuki B M, Smith M E, Barralet J E, Wright A J. Synthesis and structure of a calcium polyphosphate with a unique criss-cross arrangement of helical phosphate chains. Chem Mater 2005; 17:4642-4646), or the described calcium-polyphosphate complex (Müller W E G, Wang X H, Diehl-Seifert B, Kropf K, Schloßmacher U, Lieberwirth I, Glasser G, Wiens M, Schröder H C. Inorganic polymeric phosphate/polyphosphate is an inducer of alkaline phosphatase and a modulator of intracellular $Ca^{2+}$ level in osteoblasts (SaOS-2 cells) in vitro. Acta Biomater 2011; 7:2661-2671).

The new and hard polyP material according to this invention is biodegradable and displays superior morphogenetic activity, compared to the Ca-polyP salts prepared by conventional techniques.

In addition, the inventive hard Ca-polyP nanoparticles are prone to cellular uptake (even observed for larger, 600 nm particles; Zhao Y, Sun X, Zhang G, Trewyn B G, Slowing I I, Lin V S. Interaction of mesoporous silica nanoparticles with human red blood cell membranes: size and surface effects. ACS Nano 2011; 5:1366-1375) and subsequent metabolization, a property that is not possible for the free polyanionic polyP polymer.

The chain lengths of the polyP molecules can be in the range 3 to up to 1000 phosphate units. Optimal results are achieved with polyP molecules with an average chain length of approximately 200 to 20, and optimally about 30 to 50 phosphate units.

A further aspect of the invention concerns the material as obtained by one of the methods described above.

Further, the inventors demonstrate that the inventive method can be used for the preparation of hard amorphous and morphogenetically active polyP nanoparticles.

A further aspect of the invention concerns a material comprising the nanoparticles as obtained by one of the methods described above.

The technology according to this invention can be used for the fabrication of nanoparticles or for a material containing such nanoparticles to be used, preferably, in bone regeneration and repair and in dentistry.

A further aspect of the invention concerns the application of the inventive nanoparticles in drug delivery, again, preferably, in bone regeneration and repair and in dentistry, in analogy to, for example, systems described in Kwon et al. and Yang et al. (Kwon S, Singh R K, Perez R A, Abou Neel E A, Kim H W, Chrzanowski W. Silica-based mesoporous nanoparticles for controlled drug delivery. J Tissue Eng. 2013 Sep. 3; 4:2041731413503357. eCollection 2013. Yang P, Gai S, Lin J. Functionalized mesoporous silica materials for controlled drug delivery. Chem Soc Rev. 2012 May 7; 41(9):3679-98).

A further aspect of the invention concerns a material such as a crème or ointment containing such retinol/calcium-polyphosphate nanospheres (retinol/aCa-polyP-NS) obtained by one of the methods described above.

The technology according to this invention can be applied for the fabrication of nanospheres or a material containing these nanospheres, such as a crème or ointment, to be used in the treatment or prophylaxis of dermatological conditions such as inflammatory skin disorders, acne, disorders of increased cell turnover like psoriasis, skin cancers, and photoaging.

A further aspect of the invention concerns the application of the inventive nanospheres in drug delivery.

The invention will now be described further in the following preferred examples, nevertheless, without being limited thereto. For the purposes of the present invention, all references as cited herein are incorporated by reference in their entireties.

EXAMPLES

In the following examples, the inventive method described only for polyP molecules with a chain length of 30 to 50 phosphate units. Similar results can be obtained by using polyP molecules with lower and higher chain lengths, such as between 100 to 20 units.

FTIR Analyses

Figure 1:
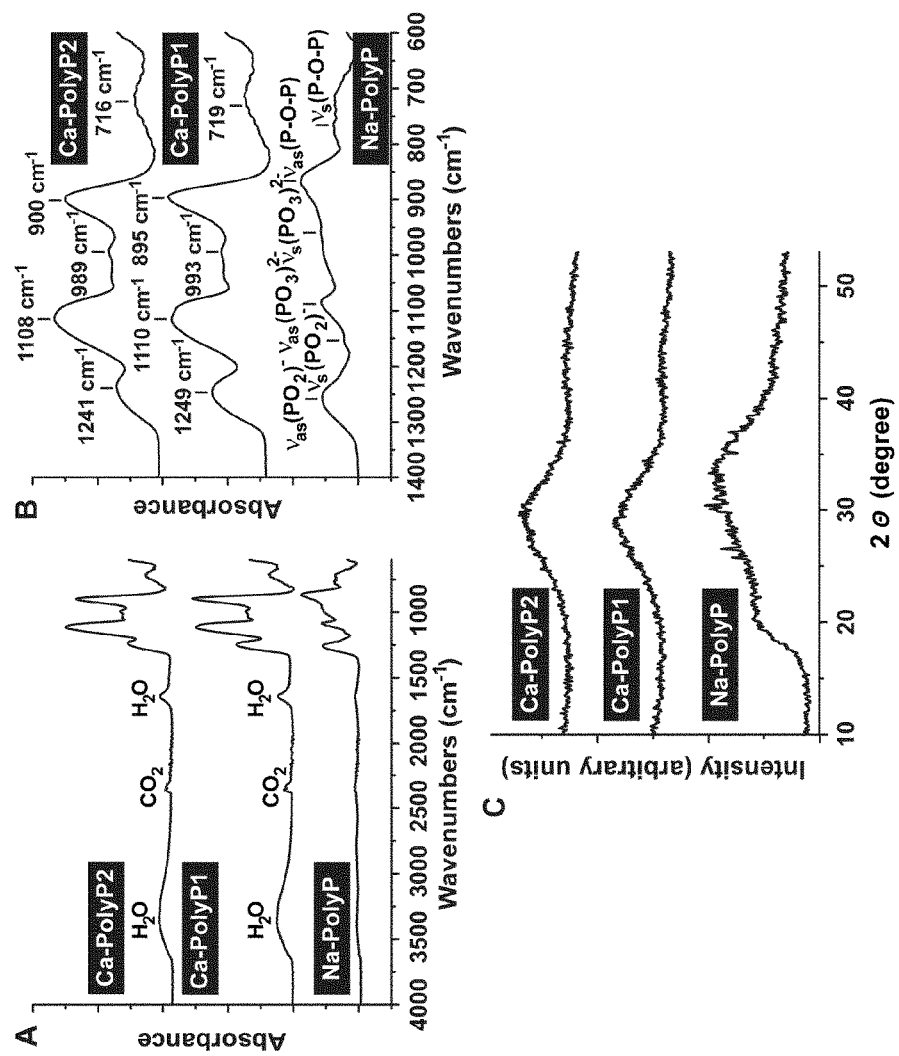
FIG. 1 shows the FTIR spectra of Na-polyP, Ca-polyP1 and Ca-polyP2; (A) wavenumbers 4000 to 600 $cm^{-1}$; (B) wavenumbers 1400 and 600 $cm^{-1}$; and (C) XRD analyses were performed with both Ca-polyP1 and Ca-polyP2; the patterns showed no sign of crystallinity, like Na-polyP.

The two phosphate materials, Ca-polyP1 and Ca-polyP2, were characterized by FTIR and compared with the spectrum obtained with Na-polyP (FIG. 1). The complete spectra between the wavenumbers 4000 and 600 $cm^{-1}$ are shown in FIG. 1A, while segments between 1400 and 600 $cm^{-1}$ are given in FIG. 1B. The band near 1250 $cm^{-1}$ is assigned to the asymmetric stretching mode of the two non-bridging oxygen atoms bonded to phosphorus atoms in the $PO_2$ metaphosphate units, $v_{as}(PO_2)^-$. The weak band at 1190 $cm^{-1}$ is the $PO_2$ symmetric stretching mode $v_s(PO_2)^-$. The absorption bands close to 1083 and 999 $cm^{-1}$ are assigned to the asymmetric and symmetric stretching modes of chain-terminating $PO_3$ groups [$v_{as}(PO_3)^{2-}$ and $v_s(PO_3)^{2-}$]. The absorption band near 864 $cm^{-1}$ is attributed to the asymmetric stretching modes of the P—O—P linkages, $v_{as}$ (P—O—P) and the partially split band centered around 763 $cm^{-1}$ is due to the symmetric stretching modes of these linkages, $v_s$ (P—O—P).

The comparison of the spectra of Na-polyP and Ca-polyP shows that the polyP features are seen in the 1300-1000 $cm^{-1}$ region. There, most of the chemical characteristics of polyP chains are found. In all three samples a similar pattern is seen, reflecting that the polyP chain backbones are not broken down during the reaction with the $Ca^{2+}$ ions. However, the peaks are shifted in the Ca-polyP1 and Ca-polyP2 samples if compared the Na-polyP spectrum. This shifting is also seen for other bands in the Ca-polyP spectra; they even increase by increasing the $Ca^{2+}$ content in the polyP sample (from Ca-polyP1 to Ca-polyP2). Moreover, it has been reported that the adsorptions bands near 1100-1000 $cm^{-1}$ are attributed to the ionic stretching mode of the P—O— group, the shifting as well as broadening of this peak of the Ca-polyP samples is attributed to the formation of P—O••$M^{+(+)}$ (where M is $Ca^{2+}$). In conclusion, the IR spectra confirm the interaction between $Ca^{2+}$ and polyP and the formation of Ca-PolyP.

XRD analyses were performed with both Ca-polyP1 and Ca-polyP2; the patterns showed no sign of crystallinity, like Na-polyP (FIG. 1C).

Morphology of polyP Samples

Figure 2:
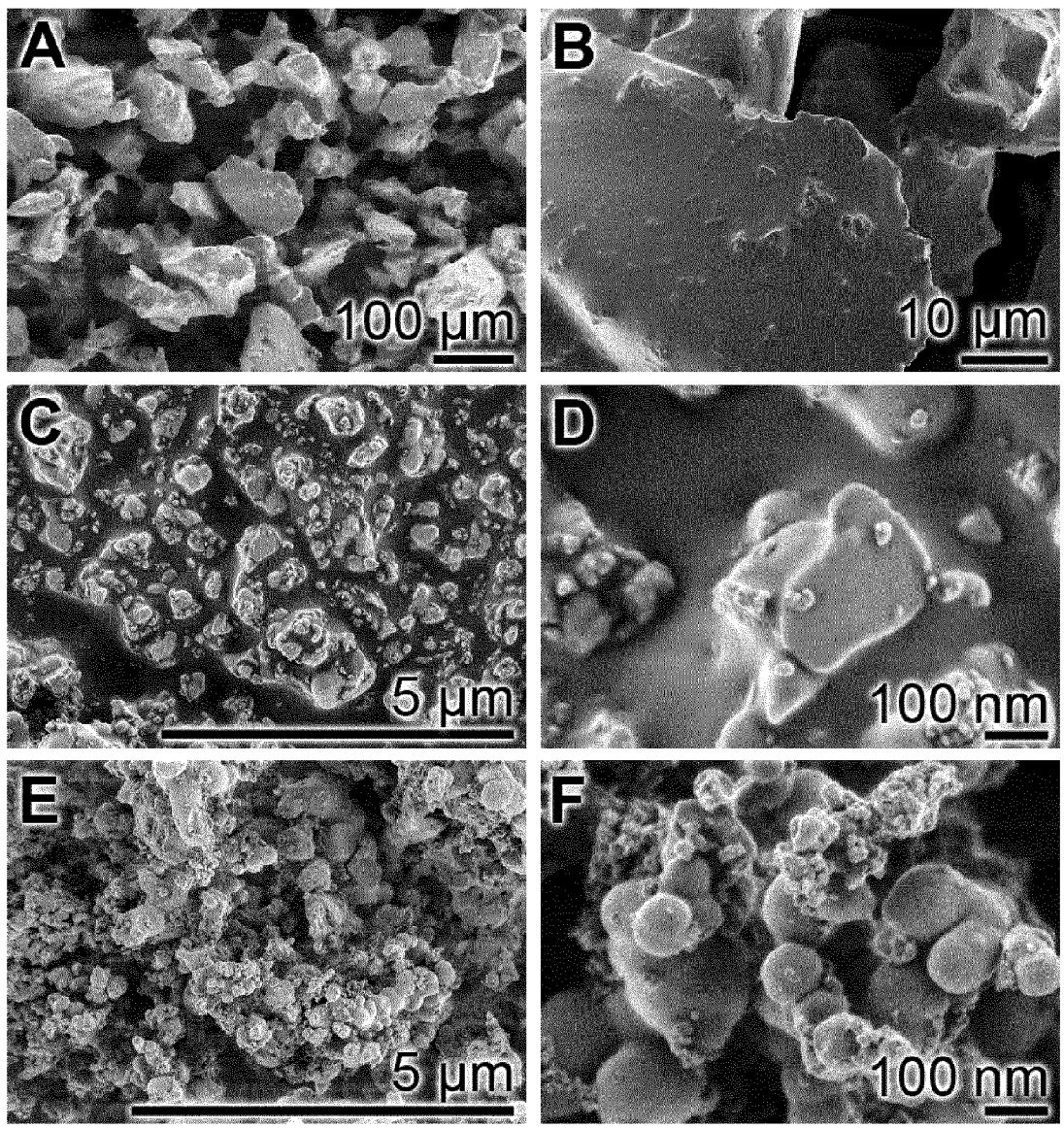
FIG. 2 shows the SEM micrographs taken from the following polyP powders: (A and B) Na-polyP, (C and D) Ca-polyP1 and (E and F) Ca-polyP2.

The three samples, Na-polyP, Ca-polyP1 and Ca-polyP2, were analyzed by SEM (FIG. 2). The Na-polyP particles, of a non-regular shapes, often show a tapered morphology (FIGS. 2A and B). The sizes of the particles vary between 1 and 300 µm with an average size of ≈100 µm. Likewise non-regular shapes show the Ca-polyP1 particles (FIGS. 2C and D). They are smaller than the Na-polyP particles with an average diameter of ≈4 μm. Even smaller are the Ca-polyP2 particles with an average diameter of ≈0.2 μm (FIGS. 2 E and F).

PolyP-Induced Mineralization of SaOS-2 Cells

Figure 3:
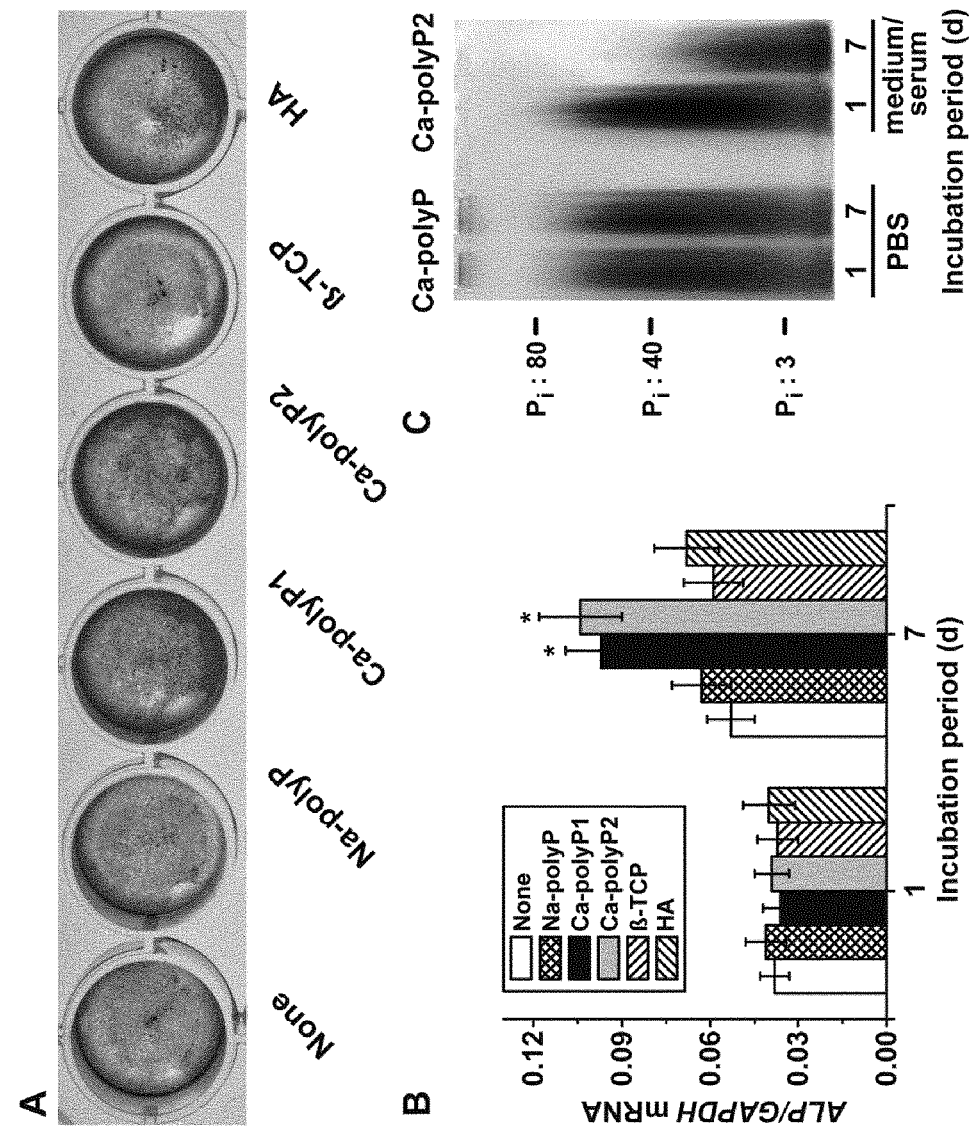
FIG. 3 shows the biological properties of the Ca-polyP material, developed here. (A) SaOS-2 cells remained without phosphate material (none), or were incubated with 10 μg/mL of Na-polyP, Ca-polyP1, Ca-polyP2, HA, or β-TCP for 7 d in the presence of the activation cocktail OC. Then the coverslips with the cells were stained with Alizarin Red S. (B) Expression level of ALP in SaOS-2 cells, in response to exposure to phosphate material. After an 1 or 7 d incubation period the cells were harvested and RNA was extracted and subjected to qRT-PCR analysis. The steady-state-levels of the ALP transcripts were measured and normalized to the expression of GAPDH. Data are expressed as mean values±SD for four independent experiments; each experiment was carried out in duplicate. Differences between the groups were evaluated using unpaired t-test. *$p<0.05$. (C) Degradation of polyP in vitro, using the 16.5% polycrylamide/7 M urea gel electrophoresis technique. The cells were incubated with 50 µg/ml of solid Ca-polyP2 either in the presence of SaOS-2 cells and medium/serum or PBS [phosphate buffered saline]; after an incubation period of 1 or 7 d, samples were taken for chain length determination. Synthetic polyP markers with an average chain length of 80, 40 and 3 units were run in parallel.

The cells were incubated with 10 μg/mL of Na-polyP, Ca-polyP1, Ca-polyP2, HA, or β-TCP in the presence of the activation cocktail OC for 7 d. Then the coverslips onto which the cells had been cultivated were removed and stained with Alizarin Red S, as described under Methods. Eye-inspection revealed that the intensity of the color reaction, which reflects the extent of minerals being present in the samples, is highest for Ca-polyP1 and for Ca-polyP2. The degree of color reaction is lower for Na-polyP, β-TCP and HA; the intensities of those samples are only slightly higher, compared to the control (FIG. 3A).

Expression Level of ALP

Since the Alizarin Red S color reaction might not be sensitive enough due to cross-reactivity with exogenously added grains, the steady-state-expression level of ALP in SaOS-2 cells was quantified by qRT-PCR. The inventors determined previously that the expression level of this enzyme is a reliable marker for the polyP-induced activation of bone cells (Müller W E G, Wang X H, Diehl-Seifert B, Kropf K, Schloßmacher U, Lieberwirth I, Glasser G, Wiens M and Schröder H C. Inorganic polymeric phosphate/polyphosphate as an inducer of alkaline phosphatase and a modulator of intracellular $Ca^{2+}$ level in osteoblasts (SaOS-2 cells) in vitro. Acta Biomaterialia 2011j; 7:2661-2671). Therefore, the inventors subjected the cells, after incubation with the different phosphate samples and in the presence of the OC activation cocktail to qRT-PCR analysis. The data revealed that at day 1 the expression level of ALP is statistically not different between the different polyphosphate samples used. However, after an incubation period of 7 d the steady-state-expression levels of ALP in the cells exposed to Ca-polyP1 and Ca-polyP2 are significantly higher (≈0.10 expression units compared to the one of the reference GAPDH) than those measured for Na-polyP, β-TCP or HA (≈0.055 expression units). The expression levels of the latter three assays are not significantly higher than the one seen in control assays (no phosphate sample added); FIG. 3B.

Hardness of the Ca-polyP2 Material

Determination of the mechanical properties (elastic modulus) of the Ca-polyP2 biopolymer was performed with a ferrule-top cantilever and found to be of ≈1.3 GPa, close to values measured for trabecular tissue that is surrounding human bone with 6.9 GPa (Zysset P K, Guo X E, Hoffler C E, Moore K E, Goldstein S A. Elastic modulus and hardness of cortical and trabecular bone lamellae measured by nanoindentation in the human femur. J Biomech 1999; 32:1005-1012).

Degradation of polyP In Vitro

In one series of experiments, the SaOS-2 cells were incubated with 50 μg/ml of solid Ca-polyP2 and incubated in the standard assay for 1 d or 7 d either in the presence of SaOS-2 cells and medium/serum or in PBS. Then samples were taken and assayed for the chain length of polyP (Lorenz B, Schröder H C. Mammalian intestinal alkaline phosphatase acts as highly active exopolyphosphatase. Biochim Biophys Acta 2001; 1547:254-261). The gels were stained with o-toluidine blue. The results (FIG. 3C) show that Ca-polyP2, added to the assays, does not undergo hydrolytic degradation during the 7 d long incubation period if dissolved in PBS. In contrast the average chain length of Ca-polyP2 drops from an average chain length of 40 to around 3 $P_i$ units if the polymer is incubated in the assays which contained SaOS-2 cells and medium/serum. This result indicates that Ca-polyP2 is prone to hydrolysis by ALP (exopolyphosphatase), but also to other polyP hydrolyzing enzymes, endophosphatases, that exist in serum.

Methods

Polyphosphate

The sodium polyphosphate (Na-polyP of an average chain of 40 phosphate units) used in the Examples has been obtained from Chemische Fabrik Budenheim (Budenheim; Germany). Na-polyphosphate (Na-polyP) with an average chain length of 30 phosphate units $(NaPO_3)_n$ can also be obtained, for example, from Merck Millipore ((#106529; Darmstadt; Germany), all-trans retinol, for example, from Sigma (#95144; ≥97.5%, $M_r$, 286.45; Sigma, Taufkirchen; Germany)

Preparation of Calcium Polyphosphate Nanospheres

Ten g of Na-polyP are dissolved in 500 ml of distilled water and the pH is adjusted to 10 with 1 M NaOH. A solution of 14 g of calcium chloride dihydrate or 28 g of $CaCl_2$ in 250 ml is added slowly, dropwise (1 ml/min) to the Na-polyP solution, adjusting steadily the pH to 10 at room temperature. The suspension formed is stirred for 4 hr. Then the particles formed are collected by washing twice with ethanol while filtering through a 0.45 μm filter (e.g., Nalgene Rapid-Flow). Then the particles are dried at 50° C. or 60° C. The Ca-polyP material obtained by addition of 14 g of $CaCl_2$ is named "Ca-polyP1", and the one with 28 g of $CaCl_2$ is termed "Ca-polyP2". aCa-polyP-NP contains a ratio: phosphate:$Ca^2$=2.

Figure 4:
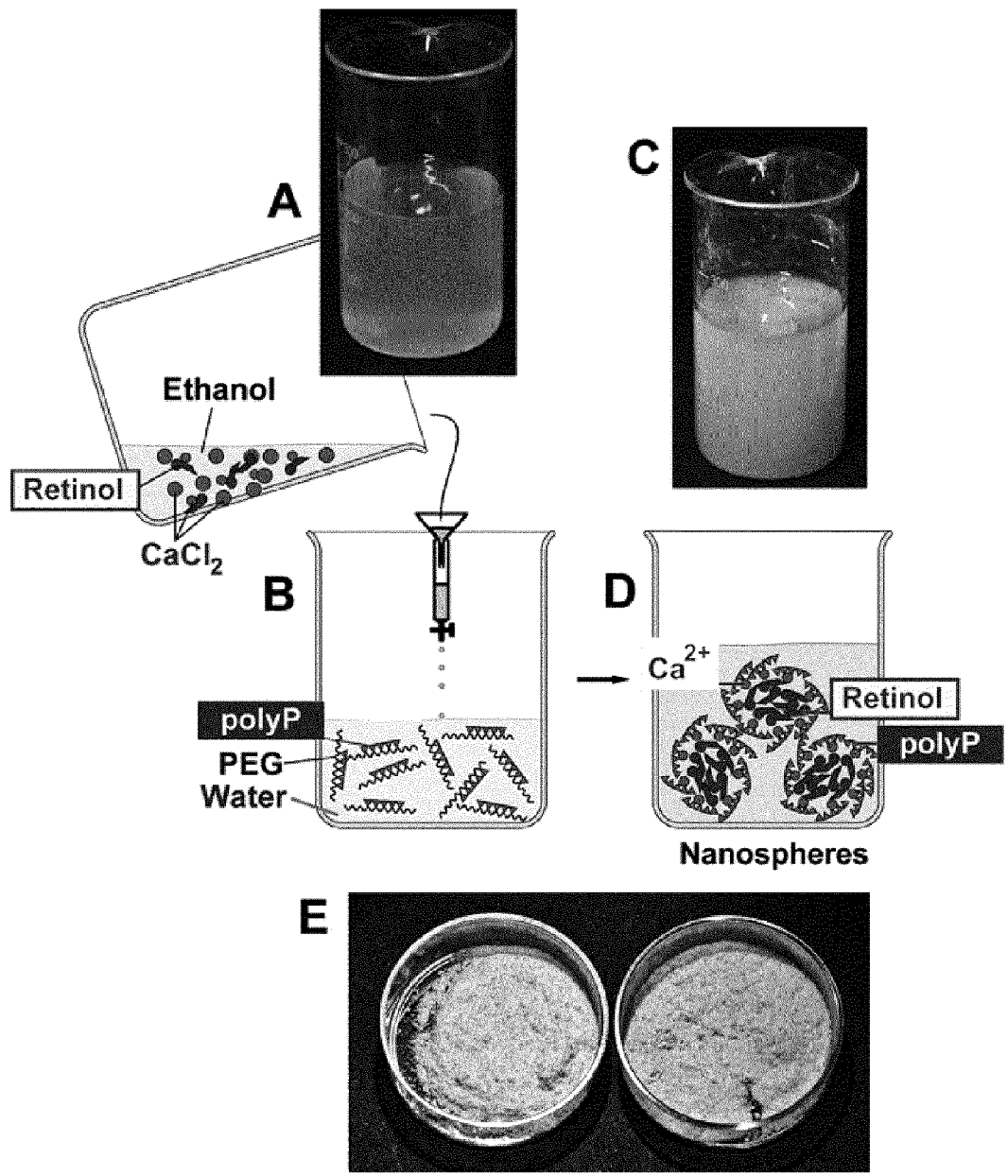
FIG. 4 shows the preparation of retinol/aCa-polyP-NSs. (A) A retinol solution was added drop-wise to (B) a Na-polyP solution, containing PEG. (C) An emulsion was formed that contained (D) the retinol/aCa-polyP-NS, composed of $Ca^{2+}$, polyP and retinol. (E) Nanospheres, lacking (left) and containing retinol (right) are shown. Further details are in "Methods".

The amorphous retinol/Ca-polyP nanospheres, retinol/aCa-polyP-NS, are prepared by a process under avoidance of light. A retinol solution (100 mg/50 ml absolute ethanol), containing 2.8 g of $CaCl_2$ (FIG. 4A), is prepared and added drop-wise to a Na-polyP solution (1 g in 100 ml water; FIG. 4B). In order to avoid a phase separation and to stabilize the emulsion 2 g of poly(ethylene glycol) [PEG] (for example: #P5413; Sigma-Aldrich; average mol wt 8,000) are added to the Na-polyP solution. The emulsion formed (FIG. 4C) is stirred for 6 h. The particles formed (FIG. 4D) are collected by filtration and washed three times with water to remove excess of calcium ions and unreacted components. Then the particles are dried at room temperature overnight; in contrast to the nanospheres, formed without retinol, those which contain this ingredient have a light yellow color (FIG. 4E).

The preparation of the aCa-polyP-NP has been described (Müller W E G, Tolba E, Schröder H C, Wang S F, Glaßer G, Muñoz-Espí R, Link T, Wang X H. A new polyphosphate calcium material with morphogenetic activity. Materials Lett 2015, in press). These nanoparticles are prepared by precipitation of Na-polyP with $Ca^{2+}$ in a stoichiometric ratio of 1:2. The polyP nanospheres, likewise amorphous, are produced from an ethanolic solution of retinol with $CaCl_2$ (FIG. 4A) that is added to a solution of Na-polyP with PEG (FIG. 4B), during which a suspension of retinol/aCa-polyP-NS is formed (FIG. 4D). The nanospheres are collected and have a slightly yellow color, in contrast to the nanoparticles that lack retinol (FIG. 4F).

Chemical Characterization by FTIR

Fourier transformed infrared (FTIR) spectroscopy in the attenuated total reflectance (ATR) mode is applied, using, for example, the Varian 660-IR spectrometer with Golden Gate ATR auxiliary (Agilent). Spectra between the wavenumbers 4000 and 600 $cm^{-1}$ are recorded.

Scanning Electron Microscopy and Energy Dispersive X-Ray Spectroscopy

For the scanning electron microscopic (SEM) analyses, for example, a HITACHI SU 8000 can be employed at low voltage (<1 kV; analysis of near-surface organic surfaces). EDX spectroscopy can be performed, for example, with an EDAX Genesis EDX System attached to a scanning electron microscope (Nova 600 Nanolab) operating at 10 kV with a collection time of 30-45 s. Areas of approximately 10 µm² were analyzed by EDX.

XRD Analyses

X-ray diffraction (XRD) is performed using established procedures (Fischer V, Lieberwirth I, Jakob G, Landfester K, Muñoz-Espí R. Metal oxide/polymer hybrid nanoparticles with versatile functionality prepared by controlled surface crystallization. Adv Funct Mat 2013; 23:451-466).

Cells and Cell Culture Conditions

Human osteogenic sarcoma cells, SaOS-2 cells, are used for the experiments and cultivated in McCoy's medium with fetal calf serum [FCS] (Wiens M, Wang X H, Schloßmacher U, Lieberwirth I, Glasser G, Ushijima H, Schröder H C, Müller W E G. Osteogenic potential of bio-silica on human osteoblast-like (SaOS-2) cells. Calcif Tissue Intern 2010; 87:513-524). Cultivation of the cells is performed in 24-well plates; $3 \times 10^4$ cells are seeded per well. After an initial incubation period of 3 d, the cultures are supplemented either with 10 µg/mL of solid Na-polyP, supplemented with $CaCl_2$ in a 2:1 stoichiometric ratio, in order to compensate for the chelating activity of polyP as described (Müller W E G, Wang X H, Diehl-Seifert B, Kropf K, Schloßmacher U, Lieberwirth I, Glasser G, Wiens M, Schröder H C. Inorganic polymeric phosphate/polyphosphate as an inducer of alkaline phosphatase and a modulator of intracellular $Ca^{2+}$ level in osteoblasts (SaOS-2 cells) in vitro. Acta Biomaterialia 2011; 7; 2661-26719), or with the two polyP samples, prepared here, with Ca-polyP1 or with Ca-polyP2. In comparison also nano-hydroxyapatite (HA; for example: 677418 Sigma-Aldrich) or β-TCP (for example: 13204 Sigma-Aldrich) had been included in the test series. As controls none of those polymers is added. Then the cells are continued to be incubated in the presence of the osteogenic cocktail [OC], containing 10 nM dexamethasone, 5 mM β-glycerophosphate and 50 mM ascorbic acid. After a 7 d incubation period the cells are either stained with Alizarin Red S to assess the extent of mineralization (Schröder H C, Borejko A, Krasko A, Reiber A, Schwertner H, Müller W E G. Mineralization of SaOS-2 cells on enzymatically (silicatein) modified bio active osteoblast-stimulating surfaces. J Biomed Mater Res B Appl Biomater 2005; 75:387-392) or subjected to qRT-PCR [quantitative real-time RT-PCR] analysis (Wiens M, Wang X H, Schloßmacher U, Lieberwirth I, Glasser G, Ushijima H, Schröder H C, Müller W E G. Osteogenic potential of bio-silica on human osteoblast-like (SaOS-2) cells. Calcif Tissue Intern 2010; 87:513-524).

Mouse calvaria cells MC3T3-E1 cells (ATCC-CRL-2593) are used for the experiments and cultivated in a-MEM (Gibco—Invitrogen) containing 20% fetal calf serum [FCS] (Gibco). The medium contains 2 mM L-glutamine, 1 mM Na-pyruvate and 50 µg/ml of gentamycin. The cells are incubated in 25 cm² flasks or in 24-well plates (Greiner Bio-One) in an incubator 37° C. and 5% $CO_2$. Reaching 80% confluency, the cells are detached using trypsin/EDTA and continuously subcultured at a density of $5 \cdot 10^3$ cells/ml. The cells are seeded at a density of $5 \cdot 10^3$ cells/well. Medium/serum change was every 3 d.

The aCa-polyP-NP are added at the indicated concentration to the cultures, usually 3 µg/ml. Retinol is added in parallel; it is dissolved at 1 mg/ml ethanol and then diluted in DMSO [dimethyl sulfoxide] at the indicated concentrations. In one series of experiments Na-polyP, stoichiometrically complexed with $Ca^{2+}$ (molar ratio of 2:1/phosphate monomer:$Ca^{2+}$; Müller W E G, Wang X H, Diehl-Seifert B, Kropf K, Schloßmacher U, Lieberwirth I, Glasser G, Wiens M, Schröder H C. Inorganic polymeric phosphate/polyphosphate as an inducer of alkaline phosphatase and a modulator of intracellular $Ca^{2+}$ level in osteoblasts (SaOS-2 cells) in vitro. Acta Biomaterialia 2011; 7:2661-2671) is studied in parallel.

Transcripts Expression

For qRT-PCR reactions the primer pair Fwd: 5'-TGCA-GTACGAGCTGAACAGGAACA-3' (SEQ ID NO: 1) [$nt_{1141}$ to $nt_{1164}$] and Rev: 5'-TCCACCAAATGT-GAAGACGTGGGA-3' (SEQ ID NO: 2) [$nt_{1418}$ to $nt_{1395}$; PCR product length 278 bp] can be used for the quantification of the alkaline phosphatase [ALP] transcripts (accession number NM_000478.4). The expression level of the ALP can be normalized to the one of the reference gene GAPDH (glyceraldehyde 3-phosphate dehydrogenase; NM_002046.3) using the primer pair Fwd: 5'-CCGTCTA-GAAAAACCTGCC-3' (SEQ ID NO: 3) [$nt_{845}$ to $nt_{863}$] and Rev: 5'-GCCAAATTCGTTGTCATACC-3' (SEQ ID NO: 4) [$nt_{1o59}$ to $nt_{1o78}$; 215 bp].

Determination of the Hardness

The hardness of the polyphosphate material Ca-polyP2 can be determined, for example, by a ferruled optical fiber-based nanoindenter as described (Chavan D, Andres D, Iannuzzi D. Ferrule-top atomic force microscope. II. Imaging in tapping mode and at low temperature. Rev Sci Instrum 2011; 82:046107. doi: 10.1063/1.3579496).

PolyP Degradation In Vitro

In one series of experiments the SaOS-2 cells are incubated with 50 µg/ml of solid Ca-polyP or Ca-polyP2 and incubated in the standard assay for 4 d. Then samples (50 µl) are taken and assayed for the chain length of polyP (for example, see: Lorenz B, Schröder H C. Mammalian intestinal alkaline phosphatase acts as highly active exopolyphosphatase. Biochim Biophys Acta 2001; 1547:254-261). The gels are stained with o-toluidine blue.

Effect of aCa-polyP-NP and Retinol on Cell Growth

Figure 5:
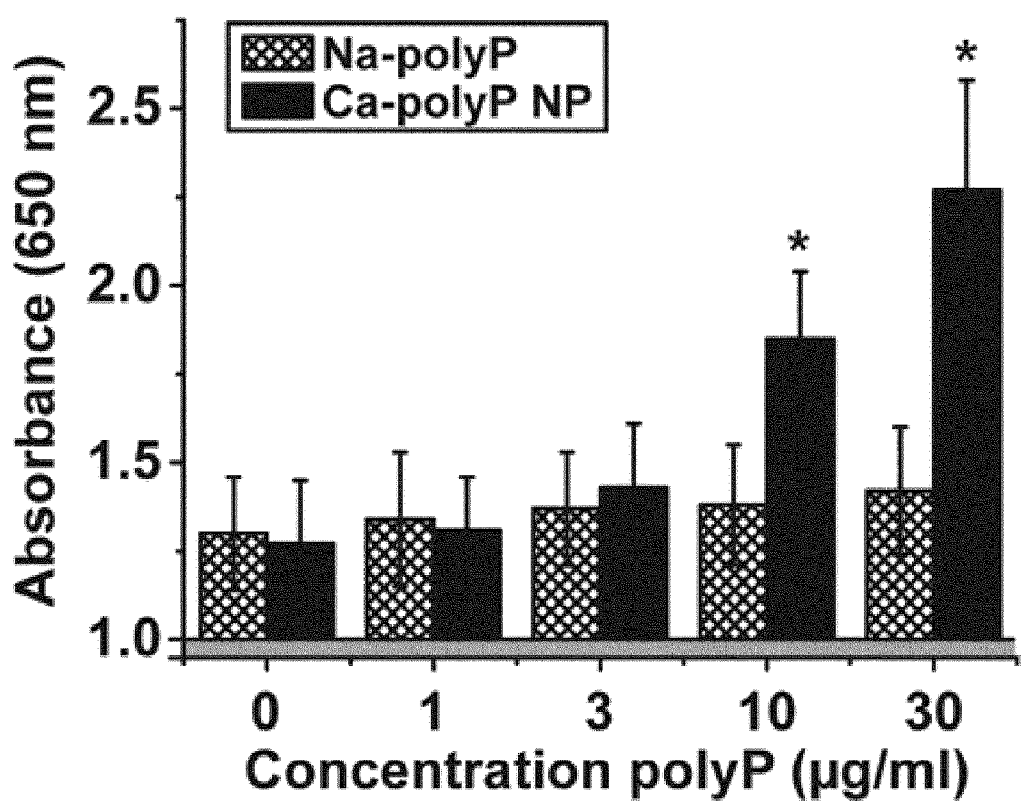
FIG. 5 shows the influence of aCa-polyP-NP versus Na-polyP on MC3T3 cell growth. The assays were composed of either Na-polyP (cross-hatched bars) or aCa-polyP-NP (filled bars) at concentrations between 1 and 30 µg/ml. After terminating the cultivation after 72 h the assays were subjected to the XTT assay and the absorbance at 650 nm was determined. Data represent means±SD of ten independent experiments (*P<0.01).

In a first series of experiments Na-polyP (complexed with $Ca^{2+}$) was tested towards aCa-polyP-NP (FIG. 5). It is seen that during the 72 h incubation period the concentration of viable cells in the assays with Na-polyP did not significantly change within a concentration range 1 to 30 µg/ml if compared with the control assays (not containing polyP). In contrast, if the aCa-polyP-NP are added instead a significant increase of the concentration of viable cells is seen at 10 µg/ml, which even increases at 30 µg/ml.

Figure 6:
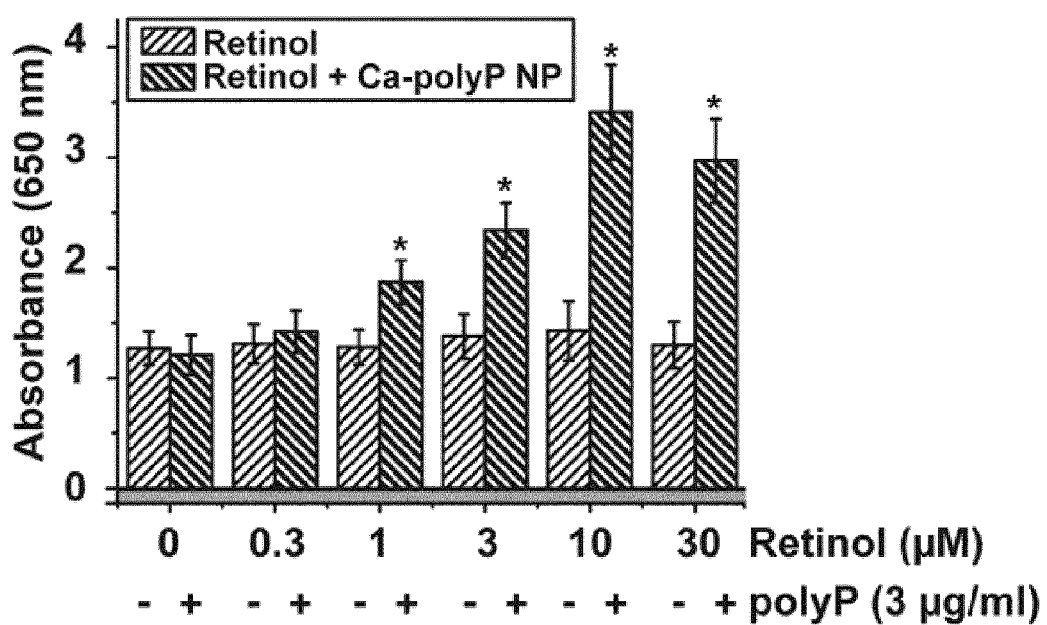
FIG. 6 shows the synergistic effect of retinol and aCa-polyP on the proliferation propensity. The concentration of aCa-polyP-NP had been kept constant (3 µg/ml) in all assays. At this concentration no effect on cell growth is seen. Addition of retinol in the range of 0.3 to 30 µM likewise did not affect the growth of the cells (left hatched bars). After co-addition of aCa-polyP-NP with retinol (right hatched bars) a strong growth-inducing effect is measured. The effect is synergistic at concentrations of retinol with higher than 1 µg/ml. *P<0.01.

Addition of retinol at concentrations between 0.3 and 30 µM and in the absence of the aCa-polyP-NP did not change significantly the growth rate of the MC3T3 cells. However, if the nanoparticles are added to the retinol-treated cells at a concentration of 3 µg/ml, a strong and significant increase in the proliferation propensity is measured (FIG. 6). The concentration of aCa-polyP-NP was kept constant with 3 µg/ml in the assays, while retinol was co-added with 0.3 to 30 µg/ml to the cells (FIG. 6). At a concentrations of ≥1 µM retinol a significant increase in the proliferation rate is seen which reaches a value of 290% at 10 µM, compared to the controls (100%; without retinol and plus/minus 3 µg/ml of aCa-polyP-NP). These findings imply that retinol and aCa-polyP-NP act synergistically on the proliferation potency of the cells.

This synergistically-acting effect of the two test components can also be followed microscopically. In the absence of any of the components the density of the MC3T3 cells after the 72 h incubation is only low. Addition of aCa-polyP-NP (3 µg/ml) alone did not change markedly the density of the cells, attached to the substrate. Likewise low is the number of cells onto the plastic surface if 10 µM retinol is added. However, if the two components [3 µg/ml of aCa-polyP-NP and 10 µM retinol] are added together the cells form an (almost) confluent cell monolayer, supporting the synergistic action of aCa-polyP-NP and retinol.

Morphology and Chemical Elemental of Ca-polyP Nanoparticles and Ca-polyP/Retinol Nanospheres The Na-polyP particles show a brick stone morphology. The size of the building bricks is >50×50×50 µm. The EDX spectra show signals, (almost) exclusively for O (oxygen), Na (sodium) and P (phosphorous); only a small peak corresponding to C (carbon) is found. In contrast to the morphology of the Na-polyP particles, the aCa-polyP-NP are spheres. After counting of 150 particles the average size (diameter) of the nanoparticles is 96±28 nm. The EDX spectra show, in addition to the elements for O and P also Ca ($K_\alpha$ peak at 3.7 keV and the $K_\beta$ peak at 4.0 keV). Only a weak signal for Na is observed; in contrast the Na peak in the Na-polyP salt is almost as high as the one for P.

The retinol/aCa-polyP-NS, produced from aCa-polyP-NP and retinol, are like the Ca-polyP nanoparticles globular. However, their size is significantly smaller with a diameter of 45±29 nm. In the EDX spectrum it is obvious that the peak, corresponding to C and originating from retinol, is significantly higher than in the spectrum of the Ca-polyP nanoparticles; the height in the EDX signal for the element C exceeds even the one for 0.

Presence of Retinol in Retinol/aCa-polyP-NS

Figure 7:
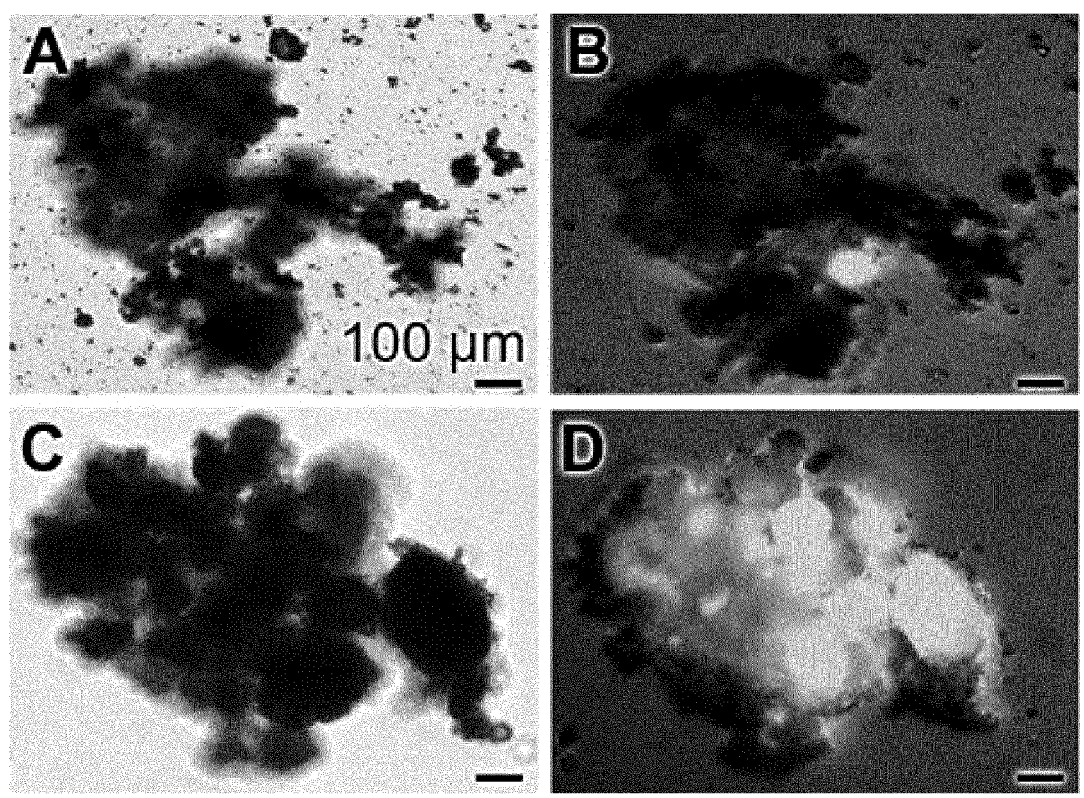
FIG. 7 shows the florescence intensities of the nanoparticles and nanospheres at an excitation of 470 nm and an emission of 525 nm. While the nanoparticles, aCa-polyP-NP (A), show only background fluorescence (B), the retinol-containing nanospheres retinol/aCa-polyP-NS (C) are lighting up with a bright green fluorescence (D).

Retinol exhibits fluorescence properties with maximum absorbance and emission at 326 nm and 520 nm (cyclohexane) (Tanumihardjo S A, Howe J A. Twice the amount of α-carotene isolated from carrots is as effective as β-carotene in maintaining the vitamin A status of Mongolian gerbils. J Nutr 2005; 135:2622-2626). In turn, retinol can be identified by fluorescence microscopy at an excitation of 470 nm and an emission of 525 nm. The images reveal that the nanospheres, retinol/aCa-polyP-NS (FIG. 7C), show a bright green fluorescence (FIG. 7D), while the nanoparticles, aCa-polyP-NP (FIG. 7A), lacking retinol, show only a slight background fluorescence (FIG. 7B).

Retinol was determined quantitatively using the $SbCl_3$-based spectroscopic technique. A suspension with 100 mg of retinol/aCa-polyP-NS nanospheres was extracted with chloroform/methanol and the released retinol determined spectrophotometrically. Applying this approach, the retinol content of the retinol/aCa-polyP-NS was determined to be 23±7% (6 parallel determinations). This figure implies that retinol undergoes an accumulation within the nanospheres that had been formed in 10% retinol-polyP starting ratio (100 mg of retinol per 1 g of polyP).

Susceptibility of polyP in the Retinol/aCa-polyP-NS Nanospheres

Figure 8:
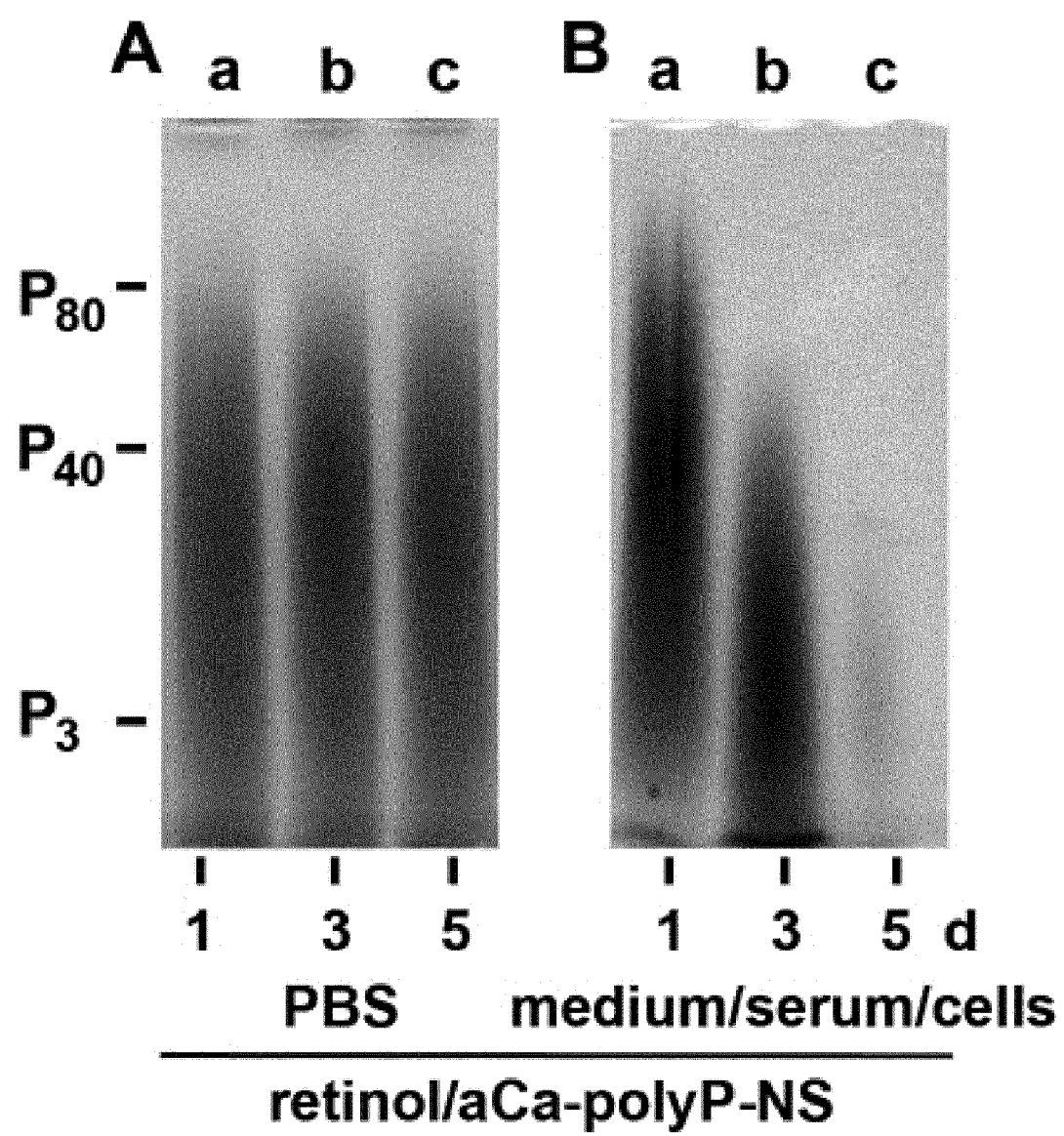
FIG. 8 shows the stability of polyP in the retinol/aCa-polyP-NS nanospheres after incubation (1 to 5 d) (A) in PBS or (B) in medium/serum supplemented with MC3T3-E1 cells in the standard incubation assay. Then aliquots were taken for chain length determination. Synthetic polyP markers with an average chain length of 80, 40 and 3 units were run in parallel.

To determine if polyP within the retinol/aCa-polyP-NS is prone to hydrolysis by phosphatases the nanospheres were incubated in PBS (FIG. 8A, lanes a-c) or in medium/serum and cells (FIG. 8B, lanes a-c) in the standard assay for 1 to 5 d. Then aliquots were taken and analyzed for the intactness of the polyP polymer. The data revealed that the average chain length of 30 $P_i$ units in the samples incubated in PBS did not change within the incubation period of 5 d (FIG. 8A, lanes a-c), while the size of polyP within the retinol/aCa-polyP-NS progressively decrease from 30 units after 1 d (FIG. 8B, lane a) to 20 units after 3 d (lane b) and even to less that 1-3 units after 5 d (lane c).

Co-Incubation of Retinol with aCa-polyP-NP on Collagen Expression

Figure 9:
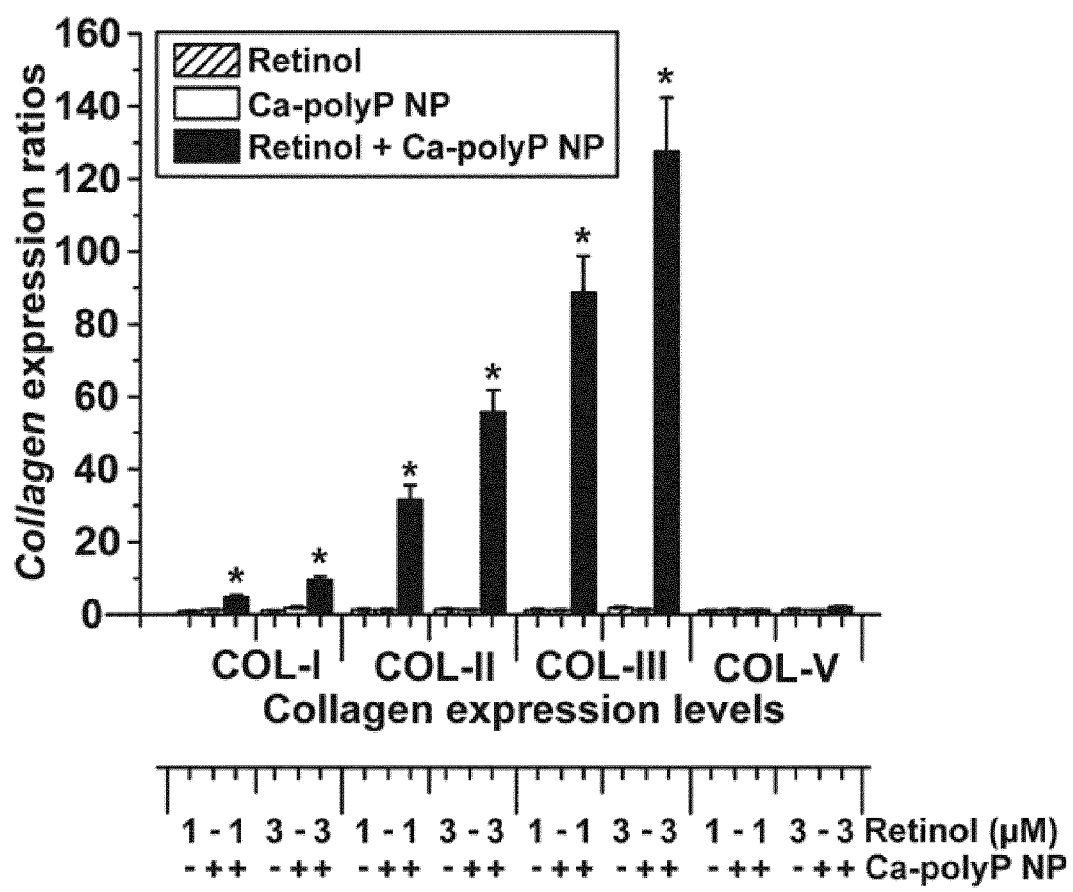
FIG. 9 shows the expression levels of the different collagen types, collagen type I (COL-I), collagen type II (COL-II), collagen type III (COL-III) and collagen type V (COL-V) in MC3T3-E1 cells exposed to either retinol or the nanoparticles aCa-polyP-NP alone or in combination; one concentration of aCa-polyP-NP (3 µg/ml) and two concentrations of retinol (1 and 3 µM) were tested. The concentrations of retinol are given in µM; aCa-polyP-NP is added at a concentration of 3 µg/ml. After a 4 d incubation period the MC3T3-E1 cells were harvested, their RNA extracted and the steady-state-levels of collagen expression were determined by RT-qPCR using the GAPDH gene as housekeeping gene as reference. The expression values of the transcripts in the RNA from cells are given as ratios between the transcripts of treated (retinol and/or aCa-polyP-NP) to untreated cells (no additional component). The results are means from 5 parallel experiments; *P<0.01.

MC3T3-E1 cells were incubated with 3 µg/ml of aCa-polyP-NP in the absence or presence of retinol (FIG. 9). After a 5 d incubation period the cells were collected and subjected to RT-qPCR analyses. The aim of the study was to elucidate if the aCa-polyP-NP modulate the expression of the different fibrillar collagen gene for type I, type II, type III and type V. the expression of the type IV basement collagen was not included since the expression level in the MC3T3-E1 cells was, even after incubating the cells with retinol, too low.

The results are shown in FIG. 9. The expression levels of the different collagen genes are given as ratio between the levels in cells exposed to either retinol or nanoparticles alone or in combination and the level measured in cells not incubated with those components. It is seen that the expression levels of collagen type I, type II, type III or type V only slightly change between 0.95 and 1.8-fold if the two components, retinol (1 µM or 3 µM) and nanoparticles (3 µg/ml), are added separately. These increases are statistically not significant. However, if retinol is added together with 3 µg/ml of aCa-polyP-NP significant increases of the expression of the collagen type I to type III levels are seen; only the changes of collagen type V are not significant. The induction level of the different collagen genes in MC3T3-E1 cells incubated with 3 µg/ml of aCa-polyP-NP and 1 µM retinol is for collagen type I 4.8-fold and with 3 µM retinol 9.4-fold; for type II 31.7-fold with 1 µM retinol or 55.8-fold with 3 µM retinol; for type III 88.7-fold (127.4-fold) and for type V 1.3-fold (2.1-fold).

Effect of the Retinol/aCa-polyP-NS Nanospheres on Collagen Expression

Figure 10:
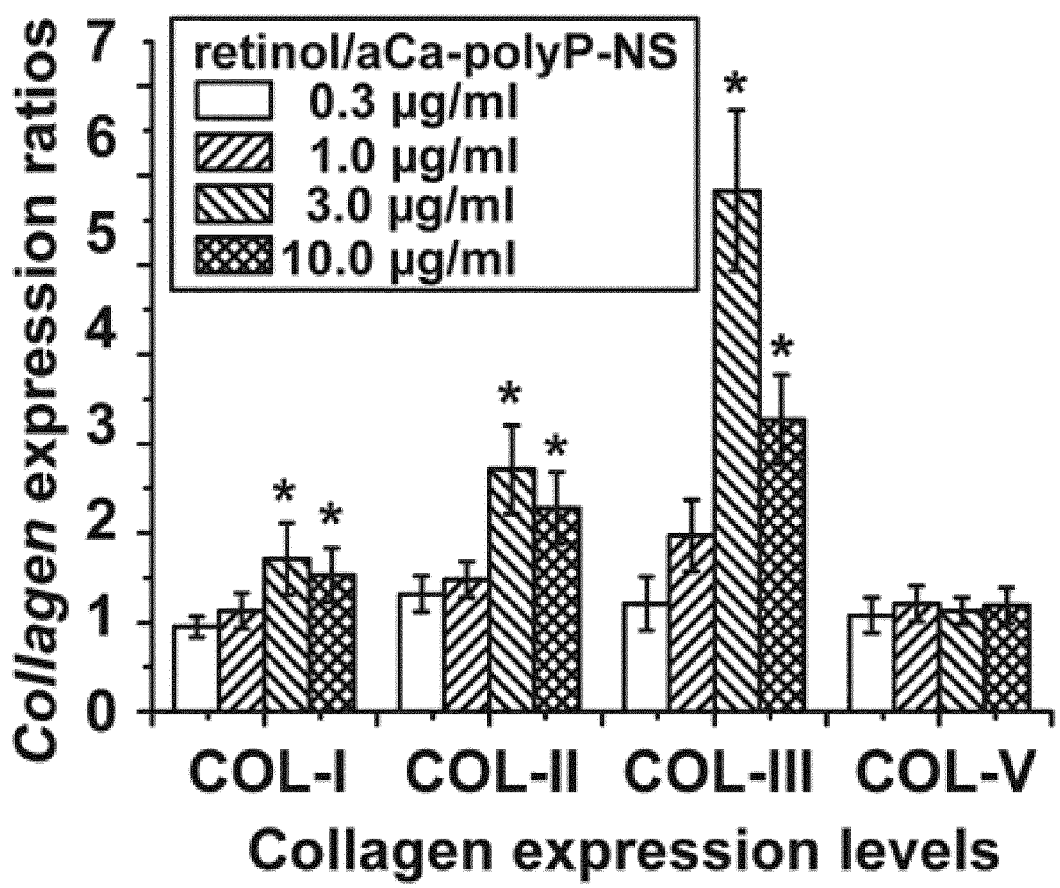
FIG. 10 shows the expression levels of the different types of collagen (COL-I, COL-II, COL-III and COL-V) in MC3T3-E1 cells. The steady-state expression values are normalized to the expression of the house-keeping gene GAPDG and are given as ratios between treated (retinol/aCa-polyP-NS) and untreated cells. *P<0.01.

In a final series of experiments the MC3T3-E1 cells were exposed to different concentrations of the retinol-containing nanospheres, retinol/aCa-polyP-NS. The expression levels are given in FIG. 10 as ratios between the collagen steady-state-values in treated cells (0.3 µg/ml to 10 µg/ml) and the values determined in untreated cells. The results show (FIG. 10), that the expression levels for collagen type I, collagen type II and of collagen type III are at concentration higher than ≥3 µg/ml retinol/aCa-polyP-NS significantly higher than the one measured for 0.3 or 1 µg/ml.

Figure 11:
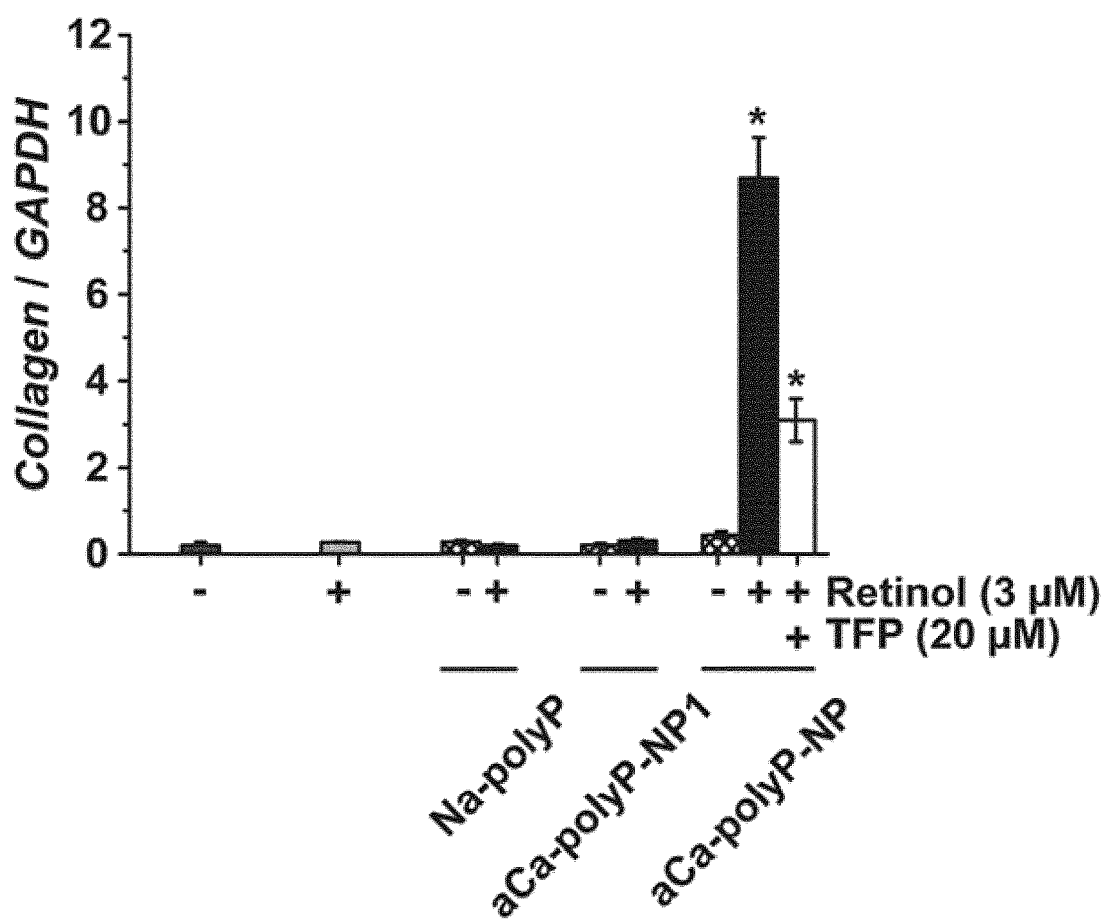
FIG. 11 shows the expression level of collagen type III gene in cells exposed to retinol alone, Na-polyP, aCa-polyP-NP1 nanoparticles (1:1 ratio between phosphate and $Ca^{2+}$) and aCa-polyP-NP (1:2 ratio between phosphate and $Ca^{2+}$) in the absence or presence of retinol. In the last series the assays were composed with retinol, aCa-polyP-NP and 20 µM of the inhibitor of the clathrin-mediated endocytosis triflupromazine (TFP). The expression of collagen type III is correlated with the house-keeping gene GAPDH. *P<0.01.

Comparative Gene Activating Effect of Retinol with Nanoparticles and Nanospheres The effect of 3 µM retinol on Na-polyP and on different nanoparticles as well as on the retinol/nanospheres was tested in a comparative way. The expression level of collagen type III was determined by RT-qPCR (FIG. 11). The expression values are correlated to the expression of the house-keeping gene GAPDH. In the absence of any additional component the collagen type III expression level was 0.17±0.02, while in the presence of 3 µM retinol the level increased significantly to 0.25±0.03. Na-polyP, stoichiometrically complexed to $Ca^{2+}$ in a molar ratio of 2:1 with the phosphate monomer forms, caused a steady-state-expression of 0.28±0.04; addition of retinol did not significantly alter the level 0.20±0.03. The nanoparticles formed from Na-polyP and $Ca^{2+}$ in an 1:1 molar ratio, aCa-polyP-NP1, caused in the absence of retinol a transcript level of 0.21±0.04 and in the presence of retinol 0.31±0.05. However, if retinol is added to the aCa-polyP-NP an increase of the expression from 0.44±0.07 to 8.7±0.93 is determined. If the inhibitor of the clathrin-mediated endocytosis triflupromazine is co-added at a 20 µM concentration the retinol-induced collagen type III expression is reduced to 3.1±0.5. To mention here, is that recently we could establish that nanoparticles fabricated in a 1:1 stoichiometric ratio between phosphate and $Ca^{2+}$ have a brick-like morphology with edge lengths of ≈4 µm, while the aCa-polyP-NP nanoparticles are globular/spherical with a size <100 nm.

Cell Proliferation—Cell Viability Assays

Cell proliferation can be determined, for example, by a colorimetric method based on the tetrazolium salt XTT (Cell Proliferation Kit II; Roche). The absorbance is determined at 650 nm and subtracted form the background values (500 nm). In the experiments described in Examples, the viable cells have been determined after 72 h.

Identification of Retinol

The green fluorescence of retinol is recorded with a fluorescence light microscope at an excitation of 470 nm and an emission of 525 nm. A quantitative analysis of retinol in the nanospheres can be performed using a colorimetric assay (Subramanyam G B, Parrish D B. Colorimetric reagents for determining vitamin A in feeds and foods. J Assoc Off Anal Chem 1976; 59:1125-1130). A suspension of 100 mg of retinol/aCa-polyP-NS is mixed with 0.45 ml of a chloroform/methanol solvent mixture (2:1; v/v) and centrifuged for 3 min at 4,200×g. Then a 0.15 ml aliquot of the organic solvent layer, containing the extracted retinol, is transferred into a reaction tube; 1 ml of 20% $SbCl_3$ solution is added drop-wise. Finally, the absorbance of the solution is measured at 620 nm immediately by using, for example, a UV-VIS spectrophotometer Varian Cary 5G UV-Vis-NIR spectrophotometer.

Enzymatic Degradation of polyP in the Retinol/aCa-polyP-NS Nanospheres

A suspension of 50 µg/ml of retinol/aCa-polyP-NS is dissolved/suspended either in PBS [phosphate buffered saline] or in medium/serum, containing MC3T3-E1 cells and incubated for 1 d, 3 d or 5 d at 37° C. Finally aliquots of 50 µl are taken, kept at ≈pH 3, and assayed for the chain length of polyP (for example, see: Lorenz B, Schröder H C. Mammalian intestinal alkaline phosphatase acts as highly active exopolyphosphatase. Biochim Biophys Acta 2001; 1547:254-261). The gels can be stained, for example, with o-toluidine blue.

Reverse Transcription-Quantitative Real-Time PCR Analyses

The technique of reverse transcription-quantitative real-time polymerase chain reaction (RT-qPCR) can be applied to determine the gene expression level of the different types of collagens in the MC3T3-E1 cells. The cells are incubated in medium/serum for 5 d in the absence or presence of retinol, aCa-polyP-NP or retinol/aCa-polyP-NS, as indicated with the respective experiment described under Examples. Then the cells are collected and the isolated RNA is subjected to RT-qPCR. The following primer pairs, matching with the respective mouse collagen types, can be used. Collagen type I alpha 1 (Mus Col1a1; NM_007742) Fwd: 5'-TACATCA-GCCCGAACCCCAAG-3' (SEQ ID NO. 5) [$nt_{4003}$ to $nt_{4023}$] and Rev: 5'-GGTGGACATTAGGCGCAGGAAG-3' (SEQ ID NO. 6) [$nt_{4146}$ to $nt_{4125}$; product size 144 bp]; type II alpha 2 (Mus Col1a2; NM_007743) Fwd: 5'-AACAC-CCCAGCGAAGAACTCATAC-3' (SEQ ID NO. 7) [$nt_{3789}$ to $nt_{3812}$] and Rev: 5'-TTCCTTGGAGGACACCCCTTC-TAC-3' (SEQ ID NO. 8) [$nt_{3908}$ to $nt_{3885}$; size 120 bp]; type III, alpha 1 (Mus Col3a1; NM_009930) Fwd: 5'-GCT-GTTTCAACCACCCAATACAGG-3' (SEQ ID NO. 9) [$nt_{4764}$ to $nt_{4787}$] and Rev: 5'-CTGGTGAATGAGTATGAC-CGTTGC-3' (SEQ ID NO. 10) [$nt_{4941}$ to $nt_{4918}$; size 178 bp]; type IV, alpha 1 (Mus Col4a1; NM_009931) Fwd: 5'-AACGTCTGCAACTTCGCCTCC-3' (SEQ ID NO. 11) [$nt_{4752}$ to $nt_{4772}$] and Rev: 5'-TGCTTCACAAACCGCA-CACC-3' (SEQ ID NO. 12) [$nt_{4886}$ to $nt_{4867}$; size 135 bp]; and type V, alpha 1 (Mus Col5a1; NM_015734) Fwd: 5'-AGTCCCTTCCTGAAGCCTGTCC-3' (SEQ ID NO. 13) [$nt_{7110}$ to $nt_{7131}$] and Rev: 5'-GCACACACACAGAGATT-AGCACC-3' (SEQ ID NO. 14) [$nt_{7265}$ to $nt_{7243}$; size 156 bp]. As the reference gene the GAPDH can be used [glyceraldehyde 3-phosphate dehydrogenase (Mus GAPDH; NM_008084) Fwd: 5'-TCACGGCAAATTCAACGGCAC-3' (SEQ ID NO. 15) [$nt_{200}$ to $nt_{220}$] and Rev: 5'-AGACTC-CACGACATACTCAGCAC-3' (SEQ ID NO. 16) [$nt_{338}$ to $nt_{316}$; size 139 bp]. The amplification can be performed, for example, in an iCycler (Bio-Rad) with the respective iCycler software. After determination of the $C_t$ values the expression of the respective transcripts is calculated.

In the Examples, the expression levels of the respective collagen genes have been determined and the values measured for the genes in cells, not exposed to either retinol or the nanoparticles/nanospheres, have been set to 1. Then the ratios between the levels in the cells, exposed to retinol or the nanoparticles/nanospheres alone or together, have been calculated and plotted.

Statistical Analysis

The results can be statistically evaluated using the paired Student's t-test.

The invention claimed is:

1. A method for the production of solid, degradable amorphous polyphosphate nanospheres having calcium counterions, wherein said method comprises the steps of:
   i) dissolving a polyphosphate salt in an aqueous solvent to create a solution and adjusting the pH value of the solution to an alkaline value,
   ii) adding a calcium salt solution to said polyphosphate salt solution, and adjusting the pH value to an alkaline value, wherein amorphous polyphosphate nanospheres are formed under the alkaline pH,
   iii) optionally, washing with a solvent and
   iv) collecting the nanospheres formed,
   wherein steps i) to iii) are performed at ambient temperature, and
   wherein said nanospheres have a hardness between 0.8 GPa and 1.8 GPa, and is morphogenetically active.

2. The method, according to claim 1, used to prepare degradable amorphous retinoid/calcium-polyphosphate (Ca-polyP) nanospheres, wherein
   a) in step i) a lubricating coating material is co-dissolved in said aqueous solvent,
   b) in step ii) a retinoid salt is co-dissolved in said solvent, and
   c) nanospheres as formed are collected.

3. The method according to claim 2, wherein the said retinoid is retinol.

4. The method according to claim 2, wherein the retinoid/Ca-polyp nanospheres are obtained by addition of one part of a solution containing 2 g/L of retinol and 56 g/L of calcium chloride in absolute ethanol to two parts of a solution containing 10 g/L of sodium polyphosphate and 20 g/L of poly(ethylene glycol) in water.

5. The method according to claim 2, wherein said retinoid/Ca-polyP nanospheres are obtained in an essentially homogenous size suitable for cellular uptake by clathrin-mediated endocytosis.

6. The method, according to claim 2, wherein in step i) the lubricating coating is a poly(ethylene glycol) polymer.

7. The method, according to claim 2, wherein the retinoid/Ca-polyP nanospheres are formulated for use in dermatology.

8. The method, according to claim 7, wherein the retinoid/Ca-polyP nanospheres are formulated as a crème or ointment.

9. The method according to claim 1, wherein said calcium salt is calcium chloride.

10. The method according to claim 1, wherein said polyphosphate salt is sodium polyphosphate.

11. The method according to claim 1, wherein the polyphosphate has a chain length of about 3 to about 1000 phosphate units.

12. The method according to claim 1, wherein the pH is adjusted to 10.

13. The method according to claim 1, wherein the polyphosphate salt is sodium polyphosphate and the calcium salt is calcium chloride at a stoichiometric ratio of 0.1 to 10 (phosphate to calcium).

14. The method according to claim 1, wherein the calcium salt solution is a solution containing 14 g/L of calcium chloride or 28 g/L of calcium chloride and the polyphosphate salt solution is a solution containing 10 g/L of sodium polyphosphate.

15. The method according to claim 1, wherein an emulsifier is added to the polyphosphate solution in order to avoid phase separation.

16. The method according to claim 1, further comprising the step of producing hard amorphous and morphogenetically active polyphosphate nanospheres, and/or a material containing such nanospheres.

17. The method, according to claim 1, wherein the aqueous solvent is water.

18. The method, according to claim 1, wherein the solid, degradable amorphous nanospheres are formulated for use in dermatology or dentistry or for regenerating bone.

* * * * *

SEQUENCE LISTING

```
<160> NUMBER OF SEQ ID NOS: 16

<210> SEQ ID NO 1
<211> LENGTH: 24
<212> TYPE: DNA
<213> ORGANISM: Homo sapiens

<400> SEQUENCE: 1
tgcagtacga gctgaacagg aaca                                        24

<210> SEQ ID NO 2
<211> LENGTH: 24
<212> TYPE: DNA
<213> ORGANISM: Homo sapiens

<400> SEQUENCE: 2
tccaccaaat gtgaagacgt ggga                                        24
```

<210> SEQ ID NO 3
<211> LENGTH: 19
<212> TYPE: DNA
<213> ORGANISM: Homo sapiens

<400> SEQUENCE: 3
ccgtctagaa aaacctgcc                                               19

<210> SEQ ID NO 4
<211> LENGTH: 20
<212> TYPE: DNA
<213> ORGANISM: Homo sapiens

<400> SEQUENCE: 4
gccaaattcg ttgtcatacc                                              20

<210> SEQ ID NO 5
<211> LENGTH: 21
<212> TYPE: DNA
<213> ORGANISM: Mus musculus

<400> SEQUENCE: 5
tacatcagcc cgaaccccaa g                                            21

<210> SEQ ID NO 6
<211> LENGTH: 22
<212> TYPE: DNA
<213> ORGANISM: Mus musculus

<400> SEQUENCE: 6
ggtggacatt aggcgcagga ag                                           22

<210> SEQ ID NO 7
<211> LENGTH: 24
<212> TYPE: DNA
<213> ORGANISM: Mus musculus

<400> SEQUENCE: 7
aacaccccag cgaagaactc atac                                         24

<210> SEQ ID NO 8
<211> LENGTH: 24
<212> TYPE: DNA
<213> ORGANISM: Mus musculus

<400> SEQUENCE: 8
ttccttggag gacacccctt ctac                                         24

<210> SEQ ID NO 9
<211> LENGTH: 24
<212> TYPE: DNA
<213> ORGANISM: Mus musculus

<400> SEQUENCE: 9
gctgtttcaa ccacccaata cagg                                         24

<210> SEQ ID NO 10
<211> LENGTH: 24
<212> TYPE: DNA
<213> ORGANISM: Mus musculus

<400> SEQUENCE: 10
ctggtgaatg agtatgaccg ttgc 24

<210> SEQ ID NO 11
<211> LENGTH: 21
<212> TYPE: DNA
<213> ORGANISM: Mus musculus

<400> SEQUENCE: 11
aacgtctgca acttcgcctc c 21

<210> SEQ ID NO 12
<211> LENGTH: 20
<212> TYPE: DNA
<213> ORGANISM: Mus musculus

<400> SEQUENCE: 12
tgcttcacaa accgcacacc 20

<210> SEQ ID NO 13
<211> LENGTH: 22
<212> TYPE: DNA
<213> ORGANISM: Mus musculus

<400> SEQUENCE: 13
agtcccttcc tgaagcctgt cc 22

<210> SEQ ID NO 14
<211> LENGTH: 23
<212> TYPE: DNA
<213> ORGANISM: Mus musculus

<400> SEQUENCE: 14
gcacacacac agagattagc acc 23

<210> SEQ ID NO 15
<211> LENGTH: 21
<212> TYPE: DNA
<213> ORGANISM: Mus musculus

<400> SEQUENCE: 15
tcacggcaaa ttcaacggca c 21

<210> SEQ ID NO 16
<211> LENGTH: 23
<212> TYPE: DNA
<213> ORGANISM: Mus musculus

<400> SEQUENCE: 16
agactccacg acatactcag cac 23